United States Patent [19]
Weininger

[11] Patent Number: 5,434,796
[45] Date of Patent: Jul. 18, 1995

[54] METHOD AND APPARATUS FOR DESIGNING MOLECULES WITH DESIRED PROPERTIES BY EVOLVING SUCCESSIVE POPULATIONS

[75] Inventor: David Weininger, Santa Fe, N. Mex.

[73] Assignee: Daylight Chemical Information Systems, Inc., Irvine, Calif.

[21] Appl. No.: 84,361

[22] Filed: Jun. 30, 1993

[51] Int. Cl.⁶ ....................... G06F 17/50; G06F 15/18
[52] U.S. Cl. .................................... 364/496; 364/578; 395/13
[58] Field of Search ............... 364/578, 496, 497, 498, 364/499; 436/86, 89; 395/13

[56] References Cited

U.S. PATENT DOCUMENTS

| | | | |
|---|---|---|---|
| 4,473,890 | 9/1984 | Araki | 395/425 |
| 4,697,242 | 9/1987 | Holland et al. | 395/13 |
| 4,704,692 | 11/1987 | Ladner | 364/496 |
| 4,811,217 | 3/1989 | Tokizane et al. | 395/800 |
| 4,852,017 | 7/1989 | Hunkapiller | 364/497 |
| 4,853,871 | 8/1989 | Pantoliano et al. | 364/496 |
| 4,855,931 | 8/1989 | Saunders | 364/499 |
| 4,881,175 | 11/1989 | Ladner | 364/496 |
| 4,908,773 | 3/1990 | Pantoliano et al. | 364/496 |
| 4,935,877 | 6/1990 | Koza | 395/13 |
| 4,939,666 | 7/1990 | Hardman | 364/496 |
| 4,961,152 | 10/1990 | Davis | 395/13 |
| 4,982,338 | 1/1991 | Fujita | 364/497 |
| 5,008,831 | 4/1991 | Feldman | 364/496 |
| 5,023,802 | 6/1991 | Fujita | 364/496 |
| 5,025,388 | 6/1991 | Cramer, III et al. | 364/496 |
| 5,047,929 | 10/1991 | Fujita | 364/496 |
| 5,048,095 | 9/1991 | Bhanu et al. | 382/9 |
| 5,081,584 | 1/1992 | Omichinski et al. | 364/496 |
| 5,136,686 | 8/1992 | Koza | 395/13 |
| 5,148,513 | 9/1992 | Koza et al. | 395/13 |
| 5,235,523 | 8/1993 | Karen et al. | 364/499 |
| 5,260,882 | 11/1993 | Blanco et al. | 364/578 |
| 5,265,030 | 11/1993 | Skolnick et al. | 364/578 |
| 5,307,287 | 4/1994 | Cramer, III et al. | 364/578 |
| 5,331,573 | 7/1994 | Balaji et al. | 364/578 |
| 5,343,554 | 8/1994 | Koza et al. | 395/13 |

OTHER PUBLICATIONS

R. Carhart, et al., "Applications of Artificial Intelligence for Chemical Inference. XVII. An Approach to Computer-Assisted Elucidation of Molecular Structure", published in Journal of the American Chemical Society Oct. 1, 1975, pp. 5755-5762.

C. Hansch, "On the Stage of QSAR", published in Drug Information Journal, vol. 18, 1984, pp. 115-122.

P. Jurs, "Computer Assisted Studies of Structure-Activity Relations Using Pattern Recognition", published in Drug Information Journal, vol. 17, 1983, pp. 219-229.

D. Boyd, "Quantum Mechanics in Durg Design: Methods and Applications", published in Drug Information Journal 1983, vol. 17, pp. 121-131.

S. Unger, "Computer-Aided Drug Design in the Year 2000", published in Drug Information Journal, vol. 21, 1987, pp. 267-275.

S. Cost and S. Salzberg, "Exemplar-based Learning to Predict Protein Folding", 1990, SCAMC, Inc., pp. 114-118.

(List continued on next page.)

Primary Examiner—Ellis B. Ramirez
Assistant Examiner—Eric W. Stamber
Attorney, Agent, or Firm—Arter & Hadden

[57] ABSTRACT

A method of and apparatus are disclosed for evolving successive populations of molecular structures and evaluating each evolved structure of each population with desired physical and/or theoretical properties. An initial population of molecules is provided in terms of representations of a number of member molecules. Evaluation is performed by a fitness function, which compares the initial population and evolved generations of member representations with the set of desired properties to provide a numerical measure or value of fitness for each structure. That numerical value indicates how closely the compared member representation corresponds with the set of desired properties. The next population is generated by changing the structure of selected molecules of a population dependent upon the numerical measure of fitness, and the process repeats. Subsequent populations evolve towards ever-better fitness. The process is terminated when an acceptable molecule evolves.

40 Claims, 36 Drawing Sheets

OTHER PUBLICATIONS

J. F. Brinkly, "Spatial Anatomic Knowledge for 2-D Interactive Medical Image Segmentation and Matching", 1992 AMIA, Inc., pp. 460–464.

K. W. Hahn, et al., "Design and Synthesis of a Peptide Having Chymotrypsin-Like Esterase Activity", published in Science, vol. 248, 22 Jun. 1990, pp. 1544–1546.

R. Carhart, et al., "Atom Pairs as Molecular Features in Structure-Activity Studies: Definition and Applications", published in J. Chem. Inf. Comput. Sci. 1985, pp. 64–72.

R. Nilakantan, et al., "Topological Torsion: A New Molecualr Descriptor for SAR Applicaitons. Comparison with Other Descriptors", published in J. Chem. Inf. Comput. Sci., vol. 27, No. 2, (1987), pp. 82–85.

R. L. DesJarlais, et al., "using Shape Complementarity as an Initial Screen in Designing Ligands for a Receptor Binding Site of Known Three-Demensional Structure", published in Journal of Medical Chemistry 1988, pp. 722–729.

R. Nikakantan et al., "Ring-Based Chemical Structural Query System" published in J. Chem. Inf. Comput. Sci vol. 30, No. 1, (1990), pp. 55–58.

M. Randic, "On Characterization of Molecualr Branching", published in Journal of the American Chemical Society, vol. 97, No. 23, Nov. 12, 1975, pp. 6609–6615.

R. A. Lewis & P. M. Dean, "Automated site-directed drug design: the concept of spacer skeletons for primary structure generation", Proc. R. Soc. London, B236, 1989, pp. 125–140.

P. P. Mager, "Computer-Assisted Series Design in Chemical Synthesis of Bioactive Compounds", published in Medicinal Research Reviews, vol. 11, No. 4, (1991), pp. 375–402.

J. P. Snyder, "Computer Assisted Drug Design. Part I. Condition in the 1980s", Medicinal Research Reviews, vol. 11, No. 6 (1991), pp. 641–662.

P. N. Craig, "QSAR-Origins and Present Status: A Historical Perspective", published in the Drug Information Journal, vol. 18, (1984), pp. 123–130.

G. M. Smith, et a l., "Intermolecular Modeling Methods in Drug Design/Modeling the Mechanism of Peptide Cleavage by Themolysin", published in Drug Information Journal, vol. 18 (1984), pp. 167–178.

Y. C. Martin & K. H. Kim, "Application of Theoretical Drug Design Methodology to a Series of Diuretics", pub. in Drug Information Journal vol. 18 (1984), pp. 93–113.

F. B. Winer, "Drug Design and the CAS OnLine Substructure Search System", published in Drug Information Journal, vol. 17, (1983), pp. 277–286.

T. Legatt & A. Saltzman, "Development of a Chemical Structure Display System and its Interface with the Associated Biological Database", published in Drug Information Journal, vol. 20 (1986), pp. 51–56.

S. Borman, "New 3-D Serach and De Novo Design Techniques Aid Drug Development", published in Chemical & Engineering News. Aug. 10, 1992, pp. 18–26.

M. A. Bedau & N. H. Packard, "Measurement of Evolutionary Activity, Teleology, and Life", published in Artificial Life II, SFI Studies in the Sciences of Complexity, vol. X (1991), pp. 431–461.

P. Schuster, "Complex Optimization in an Artificial RNA World", published in Artificial Life II, Studies in the Sciences of Complexity, vol. X, (1992), pp. 277–291.

R. Nilakantan et al., "Applications to Drug Discovery", Published in American Chemical Society (1991), pp. 527–530.

$30_0$

| 0.1363 | 0.1146 | 0.1088 | 0.0868 |
|---|---|---|---|
| CH$_3$–NH$_2$ | CH$_3$–OH | NH$_2$–OH | CH$_3$–CH$_3$ |
| 0.0577 | 0.0577 | 0.0513 | 0.0000 |
| NH$_2$–SH | CH$_3$–F | CH$_3$–Cl | CH$_3$–CH$_3$ |
| 0.0000 | 0.0000 | 0.0000 | 0.0000 |
| CH$_3$–CH$_3$ | CH$_3$–CH$_3$ | CH$_3$–CH$_3$ | CH$_3$–CH$_3$ |
| 0.0000 | 0.0000 | 0.0000 | 0.0000 |
| CH$_3$–CH$_3$ | CH$_3$–OH | CH$_3$–CH$_3$ | CH$_3$–CH$_3$ |
| 0.0000 | 0.0000 | 0.0000 | 0.0000 |
| CH$_3$–CH$_3$ | CH$_3$–CH$_3$ | CH$_3$–CH$_3$ | CH$_3$–OH |

FIG. 9A  prado 4.30k DCIS   Items 1–20   Page 1

FIG. 9B

Grok 4.30m – GENERATION: 2 FITNESS:dopamine similarity

| 0.2701 | 0.2018 | 0.1889 | 0.1889 |
|---|---|---|---|
| H₃C\CH–NH₂ / HO | NH₂–CH₂–OH | NH₂–CH=O | NH₂–CH=O |
| 0.1889 | 0.1889 | 0.1889 | 0.1859 |
| NH₂–CH=O | NH₂–CH=O | NH₂–CH=O | CH₃–CH₂–NH₂ |
| 0.1753 | 0.1753 | 0.1474 | 0.1146 |
| CH₃–CH₂–OH | CH₃–CH₂–OH | NH₂–CH=CH₂ | CH₃–OH |
| 0.1119 | 0.2146 | 0.1081 | 0.0868 |
| CH₃–O–CH₃ | NH₂–CH=O–CH=CH₂ | OH–CH=O | CH₃–CH₃ |
| 0.1771 | 0.0537 | 0.0496 | 0.0496 |
| HC=CH₂\O (epoxide) | NH₂–NH₂ | NH₃ | NH₃ |

*FIG. 9C*   prado 4.30k DCIS   Items 1–20   Page 1

FIG.9d — Grok 4.30m — GENERATION: 3 FITNESS: dopamine similarity prado 4.30k DCIS   Items 1-20   Page 1

Grok 4.30m — GENERATION: 4 FITNESS:dopamine similarity
| 0.2731 | 0.2731 | 0.2731 | 0.2722 |
|---|---|---|---|
| 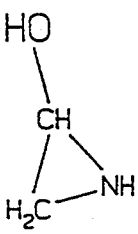 | 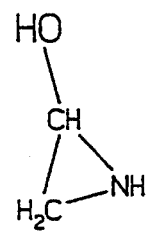 | 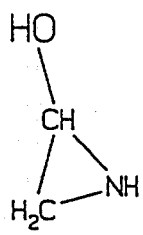 | 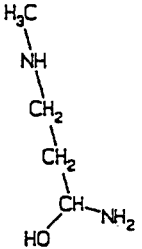 |
| 0.2580 | 0.2569 | 0.2551 | 0.2556 |
| 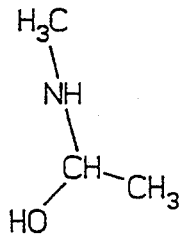 | 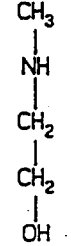 | 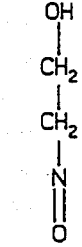 | 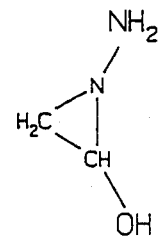 |
| 0.2519 | 0.2423 | 0.2169 | 0.2018 |
| 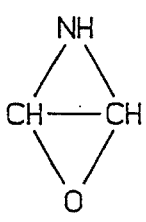 | 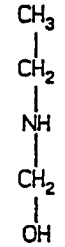 | 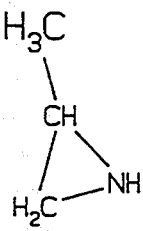 | 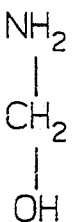 |
| 0.2018 | 0.2022 | 0.1994 | 0.1948 |
| 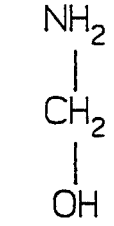 | 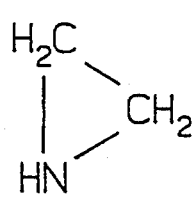 | 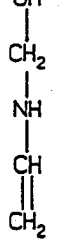 | 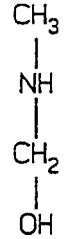 |
| 0.1859 | 0.1753 | 0.1753 | 0.1474 |
| 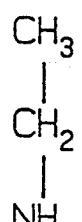 | 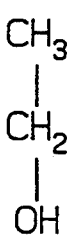 | 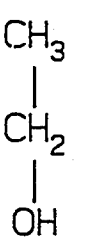 | 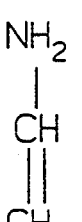 |
FIG. 9E  prado 4.30 DCIS   Items 1–20   Page 1

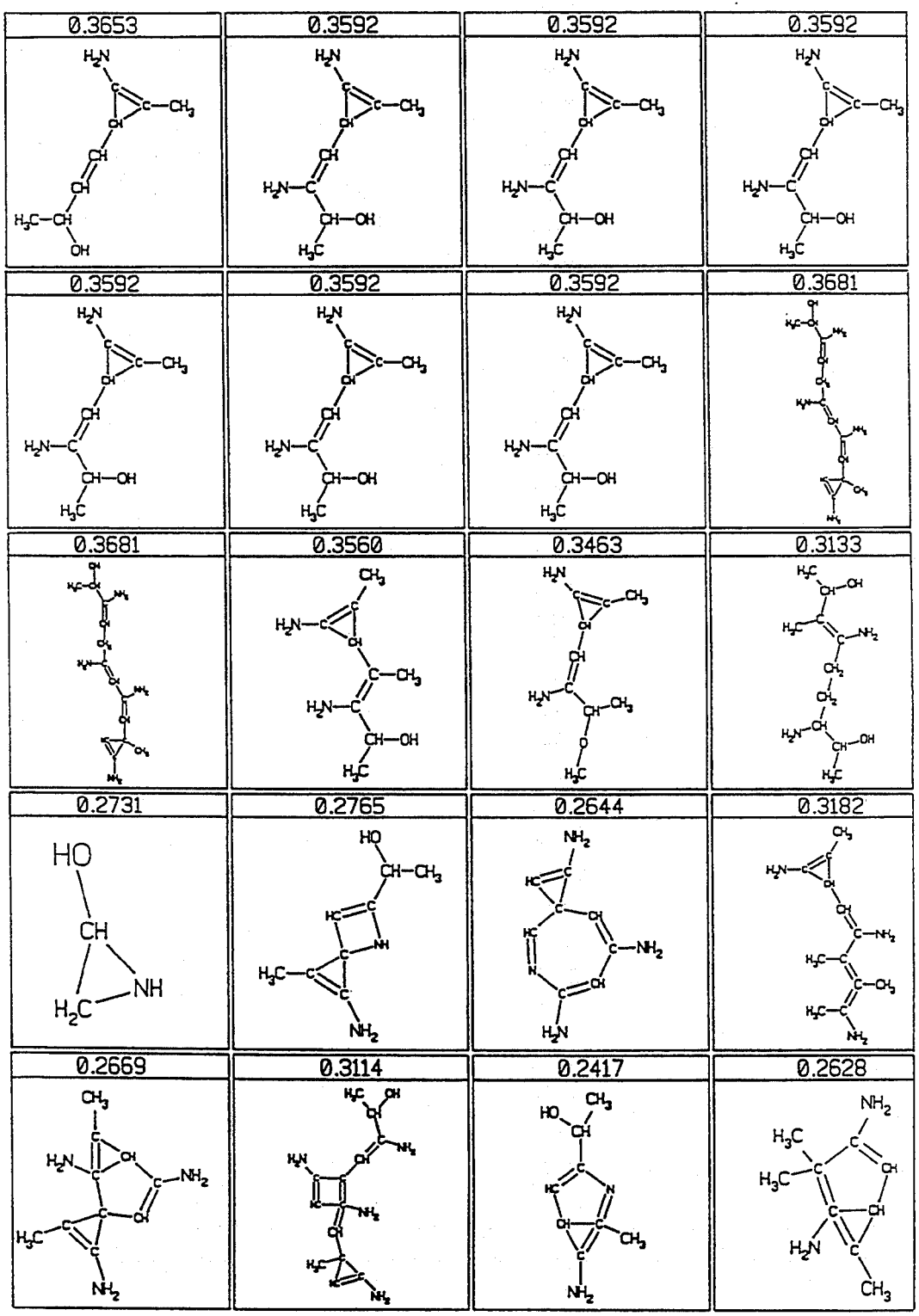
FIG. 9F prado 4.30k DCIS    Items 1-20    Page 1

Grok 4.30m – GENERATION: 20 FITNESS:dopamine similarity prado 4.30k DCIS   Items 1-20   Page 1

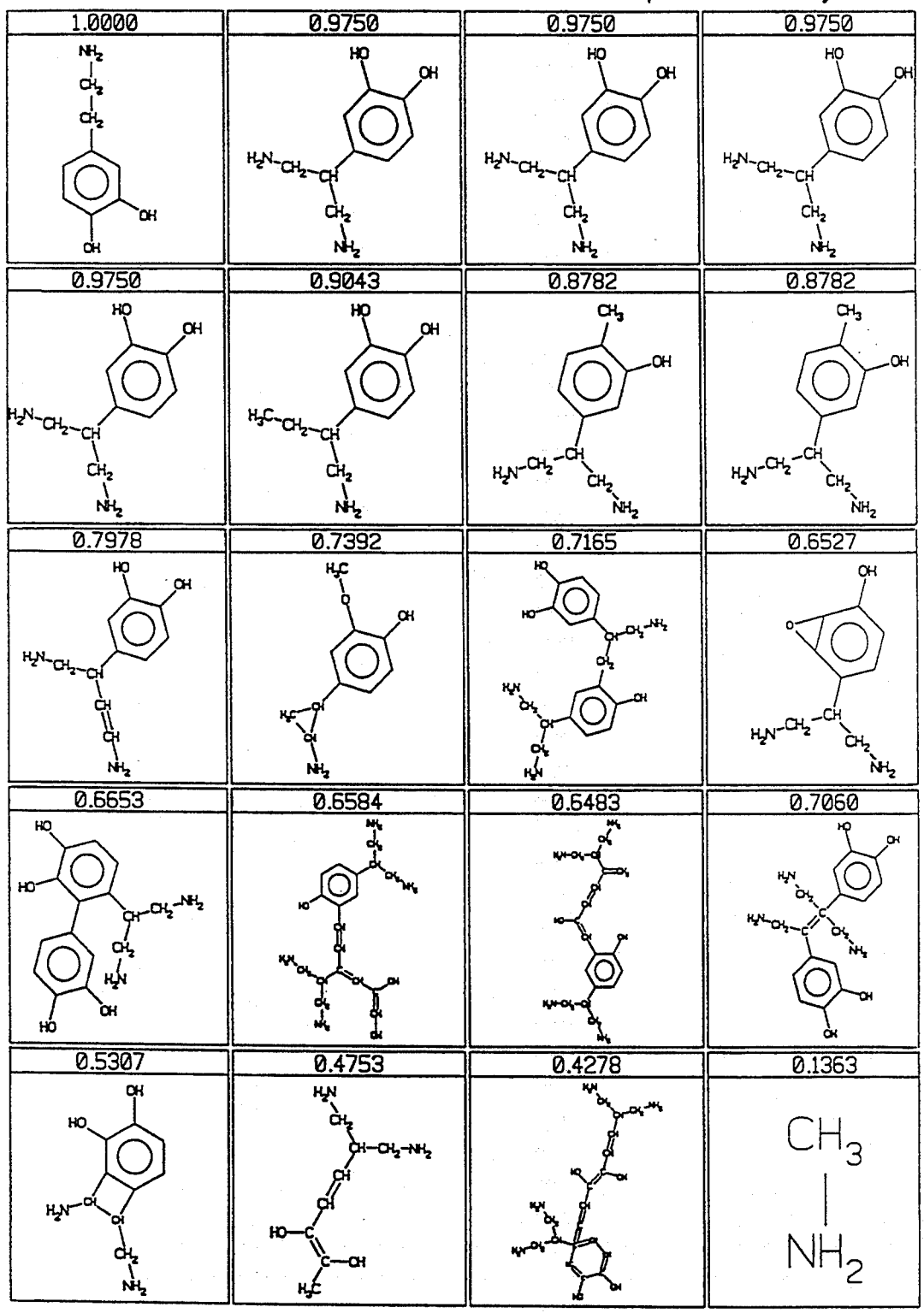
Grok 4.30m – GENERATION: 36 FITNESS:dopamine similarity
FIG. 9L    prado 4.30k DCIS    Items 1-20    Page 1

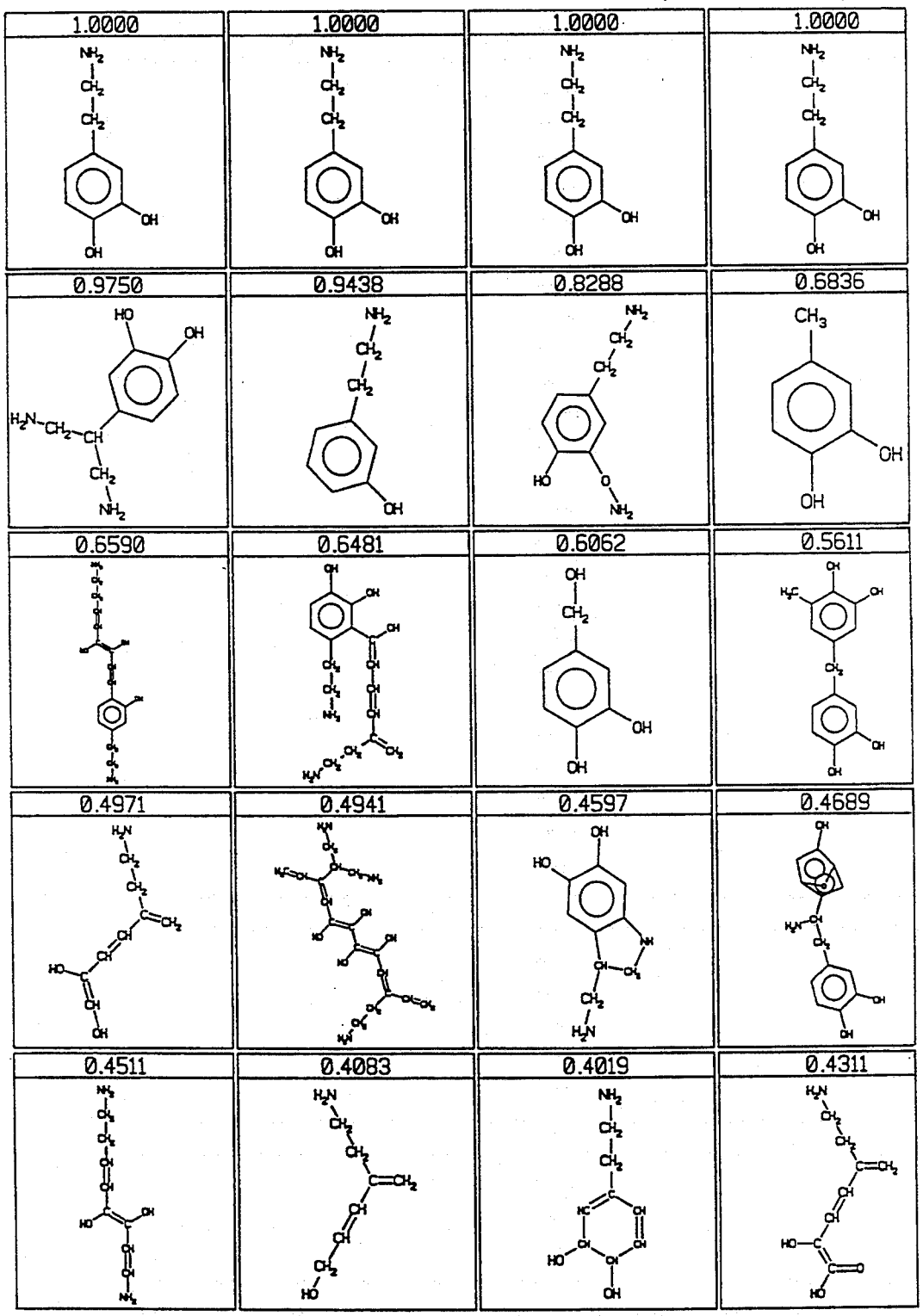
FIG.9M  prado 4.30k DCIS   Items 1-20   Page 1

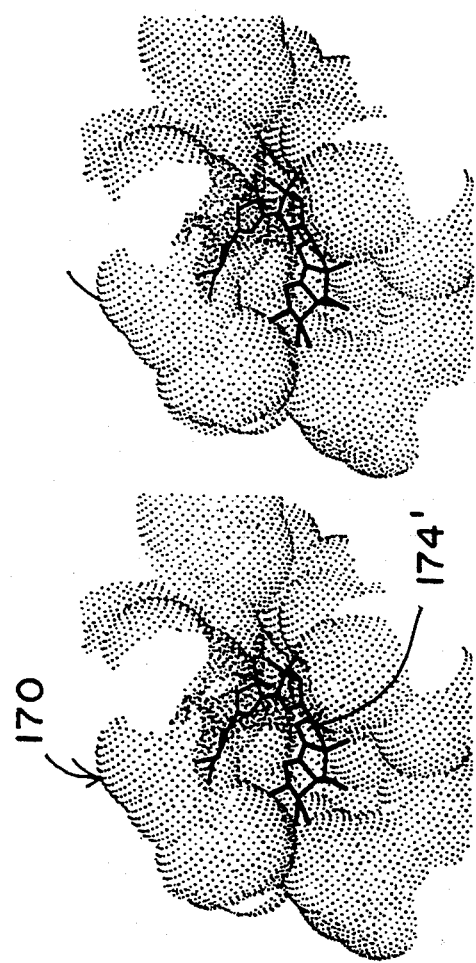

METHOD AND APPARATUS FOR DESIGNING MOLECULES WITH DESIRED PROPERTIES BY EVOLVING SUCCESSIVE POPULATIONS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to methods of and apparatus for designing chemical structures of molecules, which optimize a given mathematical function; the physical, chemical, biological and/or theoretical properties of the molecular structure; or combination thereof. This general field is known as "Computer-Assisted Molecular Design" (CAMD). When used for pharmaceutical discovery, this field is referred to as "Computer-Aided Drug Design" (CADD).

BACKGROUND OF THE INVENTION

Many approaches have been used to discover new chemicals, which are suitable for particular purposes. Although most of this methodology has been directed at drug discovery, there are examples in almost every chemical field: agrochemicals, engineering (materials), fuels, perfumes, cosmetics, photography, semiconductors, non-linearoptics, and others. The goal of chemical discovery is to find chemicals, which have specific reactivities, biological activities, chemical and/or physical properties. In general, none of the available methods are considered satisfactory.

Chemical discovery methods fall into two general categories: random screening and rational design. Random screening methods are based on the ability to screen a very large number of compounds quickly with the goal of finding one or more "lead" compounds for further testing and refinement (typically by rational design). Disadvantages of random screening are that it is extremely expensive and its probability of success is relatively low. Most companies engaged in chemical discovery use random screening because it has the best track record historically and, for many problems, it is the only feasible approach. Random screening experiments often have a minor "rational" component, e.g., chemicals screened are not truly random, but are picked to be representative of a larger set of compounds.

Rational design is based on the ability to rationalize the activity of various chemicals in terms of their molecular structure. Attempts to build a rigorous framework for this purpose date back to 1930's, e.g., see "History and Objectives of Quantitative Drug Design", by Michael S. Tute, Comprehensive Medicinal Chemistry, pub. Pergamon Press plc, ISBN 0-08-037060-8, 1990. The field developed rapidly in the early 1960's with the advent of the QSAR (Quantitative Structure-Activity Relationship) method developed by Corwin Hansch. With QSAR, the activity of a molecule is related statistically to the position and physical parameters of its functional groups. A great deal of further development has been done along these lines. Along with the ability to visualize three-dimensional (3-D) structures using computer graphics systems, this has led to the field known as "molecular modeling".

*Comprehensive Medicinal Chemistry, Vol 4 Quantitative Drug Design,* (1990) provides a good description of the current state of the art. Overall, the methods that have been developed are techniques for analysis rather than discovery. Much work has been done on predicting how a new molecule will behave. Refining lead structures has received a great amount of attention. There has been little work done on methods which suggest new molecules from an universe of all possible molecules. The reason that there are no methods for direct chemical discovery is that the problem has appeared to be intractable. Even for a very limited chemical classes, there is an enormous number of molecular structures possible.

Current successful approaches for computer assisted methods of designing molecules include the DOCK program, which is described in, "A geometric approach to macromolecule—ligand interactions", I. D. Kuntz, J. M. Blaney, S. J. Oatley, R. Langridge, T. E. Ferrin, *J. Mol. Biol.,* 161, 269 (1982); the GROW PROGRAM, which is described in "Computer design of bioactive molecules: a method for receptor-based de novo ligand design", J. B. Moon and W. J. Howe, *Proteins: Struct. Funct. Genet.,* 11, 314 (1991); and the LUDI program, which is described in "The computer program LUDI: A new method for the de novo design of enzyme inhibitors", H. J. Bohm, *J. Comp.-Aided Mol. Design,* 6, 61 (1992). DOCK selects from a database molecules, which are complementary in shape and electrostatics to a receptor or active site, and has successfully identified lead compounds in several different drug discovery projects. DOCK relies on a predetermined database of chemical structures and does not perform de novo design. LUDI uses a database of chemical fragments and heuristic rules about fragment-receptor complementarily and geometry to assemble molecules that fit a receptor or active site. GROW assembles peptides from a database of amino acid sidechains into a binding site and has successfully grown peptides that bind tightly to a few different enzymes. These three approaches are the most ambitious and successful to date, but still fall short of the goal of true de novo design of molecules with no or limited constraints, e.g., synthetic feasibility, that fit a specific receptor site optimally.

Genetic algorithms are relatively new methods which appear to be suitable for attacking global-optimization problems over high-dimensionality spaces. Genetic algorithms have been used for problems ranging from jet engine design which is described in the *Proceedings of the Third International Conference on Genetic Algorithms,* ed. James David Schaffer, pub. Morgan Kaufmann Publishers, Inc., POB 50490, Palo Alto, Calif. 94303-9953, ISBN 1-55860-066-3, 1989, to horse race handicapping which is described in the *Proceedings of the Fourth International Conference on Genetic Algorithms,* ed. Richard K. Belew, pub. Morgan Kaufmann Publishers, Inc., POB 50490, Palo Alto, Calif. 94303-9953, ISBN 1-55860-208-9, 1991. The idea behind genetic algorithms is to simulate the process of evolution. Evolution, driven via simple natural selection and genetic mechanisms, is observed to solve very hard problems, to whit, biological survival in a changing environment. In practice, this means creating a population of members (each representing solutions) which compete with each other, reproduce (subject to genetic mechanisms), and evolve better new populations (of solutions). To apply this to a given problem, one must create a "genome" representing a member of the population, invent a reproduction method which allows offspring to retain characteristics of their parents, and establish an environment which allows evolution to proceed. Two publications, *Handbook of Genetic Algorithms,* ed. Lawrence Davis, pub. Van Nostrand Reinhold, ISBN 0-442-00173-8, 1991, and *Genetic Algorithms in Search, Optimization, and Machine Learning,* by D. E. Goldberg, pub. Addison-Wesley, 1989, provide a survey of genetic algorithms.

The canonical genetic algorithm operates on fixed-sized "genomes", which are similar to those found in biological organisms. This limits its use to problems which can be mapped onto a fixed-size solution, e.g., relative positions of a fixed number of atoms in space. The canonical genetic algorithm is potentially useful for solving important chemical problems such as conformational analysis, protein sequence alignment and secondary structure prediction. Unfortunately, classical genetic algorithms are not suitable for use on problems of chemical discovery. Molecules come in all shapes and sizes and cannot be described well by a "genome" similar to that encoding biological species. As a result, the use of genetic algorithms has been limited to problems of chemical analysis, rather than discovery.

SUMMARY OF THE INVENTION

It is an object of this invention to provide a new and improved method of designing molecular structures, which optimally exhibit predefined physical and/or theoretical properties.

It is a further object of this invention is to provide a new and improved method for evolving populations of molecules having desired structures.

This invention relates to a method of evolving successive populations of molecular structures and evaluating each evolved structure of each population with desired physical and/or theoretical properties. An initial population of molecules is provided in terms of representations of a number of member molecules. Evaluation is performed by a fitness function, which compares the initial population and evolved generations of member representations with the set of desired properties to provide a numerical measure or value of fitness for each structure. That numerical value indicates how closely the compared member representation corresponds with the set of desired properties. The next population is generated by changing the structure of selected molecules of a population dependent upon the numerical measure of fitness, and the process repeats. Subsequent populations evolve towards ever-better fitness. The process is terminated when an acceptable molecule evolves.

In a further aspect of this invention, the initial population of member representations is randomly generated. Each reproduced member representation is evaluated to determine whether it is chemically stable and, if stable, it is included in the next population.

The next population is reproduced from the member representations of the present population by using various genetic mechanisms. A number of elite member representations of the present population with the best numerical values are selected to be introduced directly into the next population. Parent member representations are selected from the present population dependent upon their numerical values. One parent member representation is selected and is cloned to reproduce a single child member representation to be included within the next population. Alternatively, two parent member representations may be selected and bred to produce therefrom a single new child member representation to be included within the next population. Breeding takes selected fragments of each of the two selected parent member representations, and combines them to form the new child member representation.

Selected of the child member representations are further changed by mutating. An atom of a child member representation may be added or removed. A bond of the child member representation may be modified.

Comparison is carried out in accordance with the teachings of this invention by implementing one or more fitness functions to determine the fit of a member representation of the present population with the desired set of properties. The desired set of properties may take the form of a class of related molecules. Another fitness function performs a series of conformational analyses on each of the member representations of the present population to determine the binding energy between each of the member representations and a model of a binding site constructed in accordance with the set of desired properties. Each of the conformational analyses further determines the electrostatic interactions between the electrical charges associated with one of the member representations and the electrical charges associated with the binding site to provide a corresponding numerical value. A further fitness function synthesizes and introduces an actual molecule for each member representation of the present population, and assays the binding energy between each of the synthesized molecules and the target molecule to provide a corresponding set of numerical values. A plurality of fitness functions may be performed on each member representation of the present population to evolve the target molecule towards corresponding sets of desired properties.

BRIEF DESCRIPTION OF THE DRAWINGS

A written description setting forth the best mode presently contemplated for carrying out the present invention, and of the manner for implementing and using it, is provided by the following detailed description of an illustrative embodiment represented in the attached drawings, wherein data objects are represented by square-cornered boxes, steps or subprocesses are indicated by round-cornered boxes, and a heavy border indicates that an expanded flowchart is provided for that step or subprocess in one or more of the following drawings.

DESCRIPTION OF A PREFERRED EMBODIMENT OF THIS INVENTION

This invention is implemented in an illustrative embodiment of this invention by a plurality of computer programs, which are loaded into and executed on one or more computers. Illustratively, the computer may take the form of a computer work station such as a SGI Crimson R4000. This invention provides a powerful tool or method for determining the molecular structure of any chemical compound with desired physical and/or theoretical properties, but has particular utility for the design of drugs.

Figure 1:
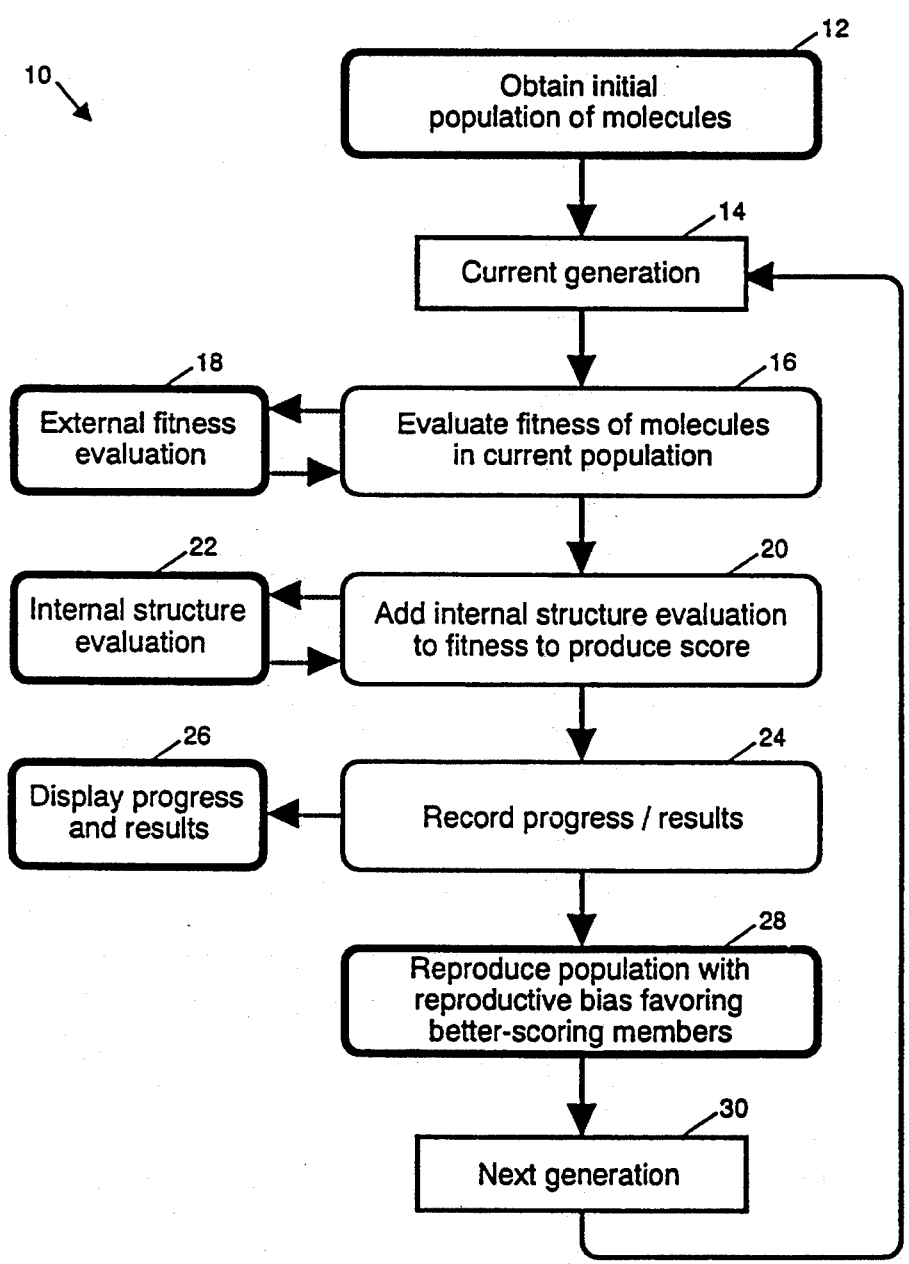
FIG. 1 is a high level flow diagram of the method of evolving successive populations of molecules, evaluating each molecule of a given population by use of a fitness function to provide an indication of how well a particular molecule fits a desired set of physical and/or theoretical properties, before evolving the next population of molecules based on the fit indication in accordance with the teachings of this invention.
Figure 9B:
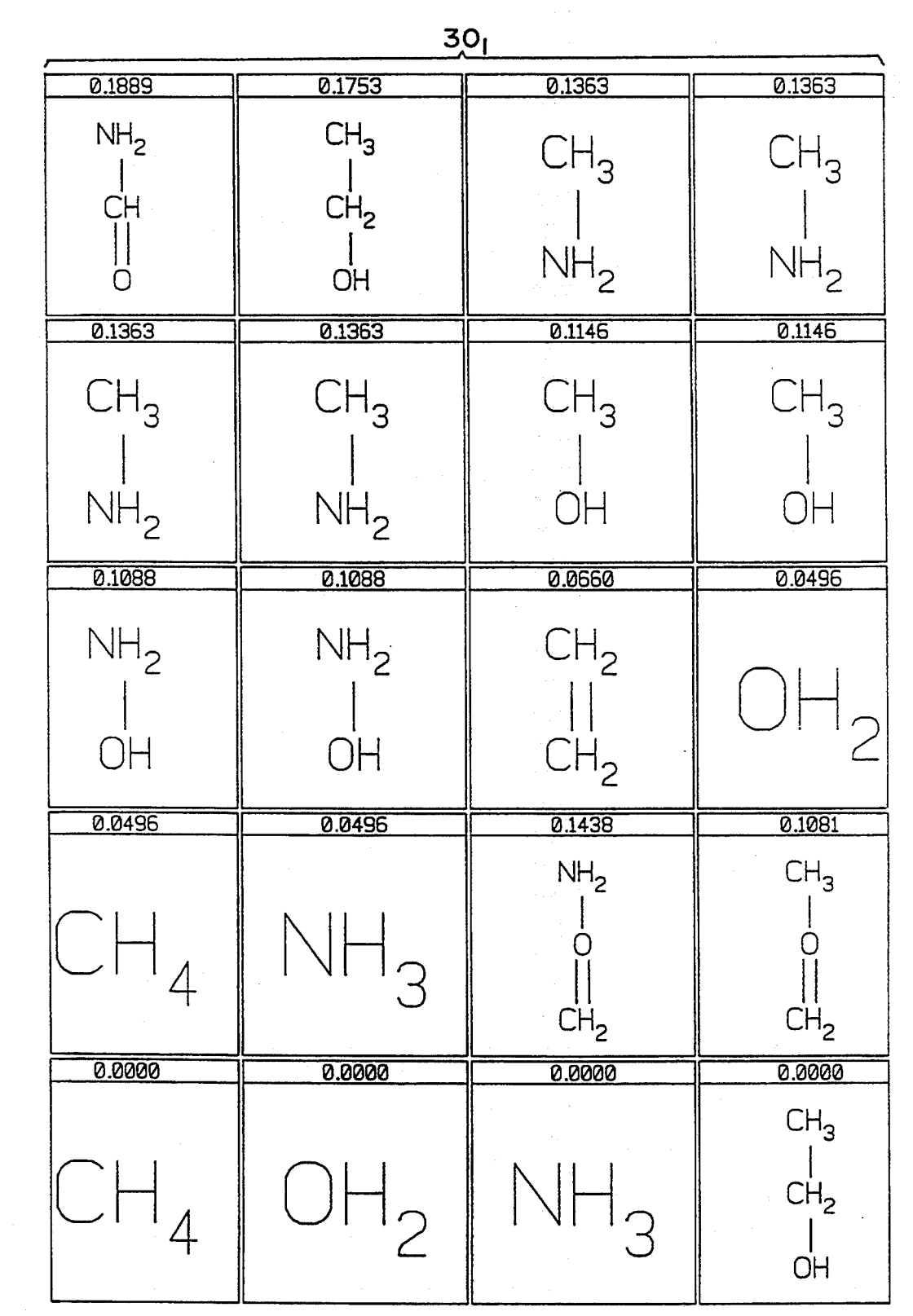
Figure 9G:
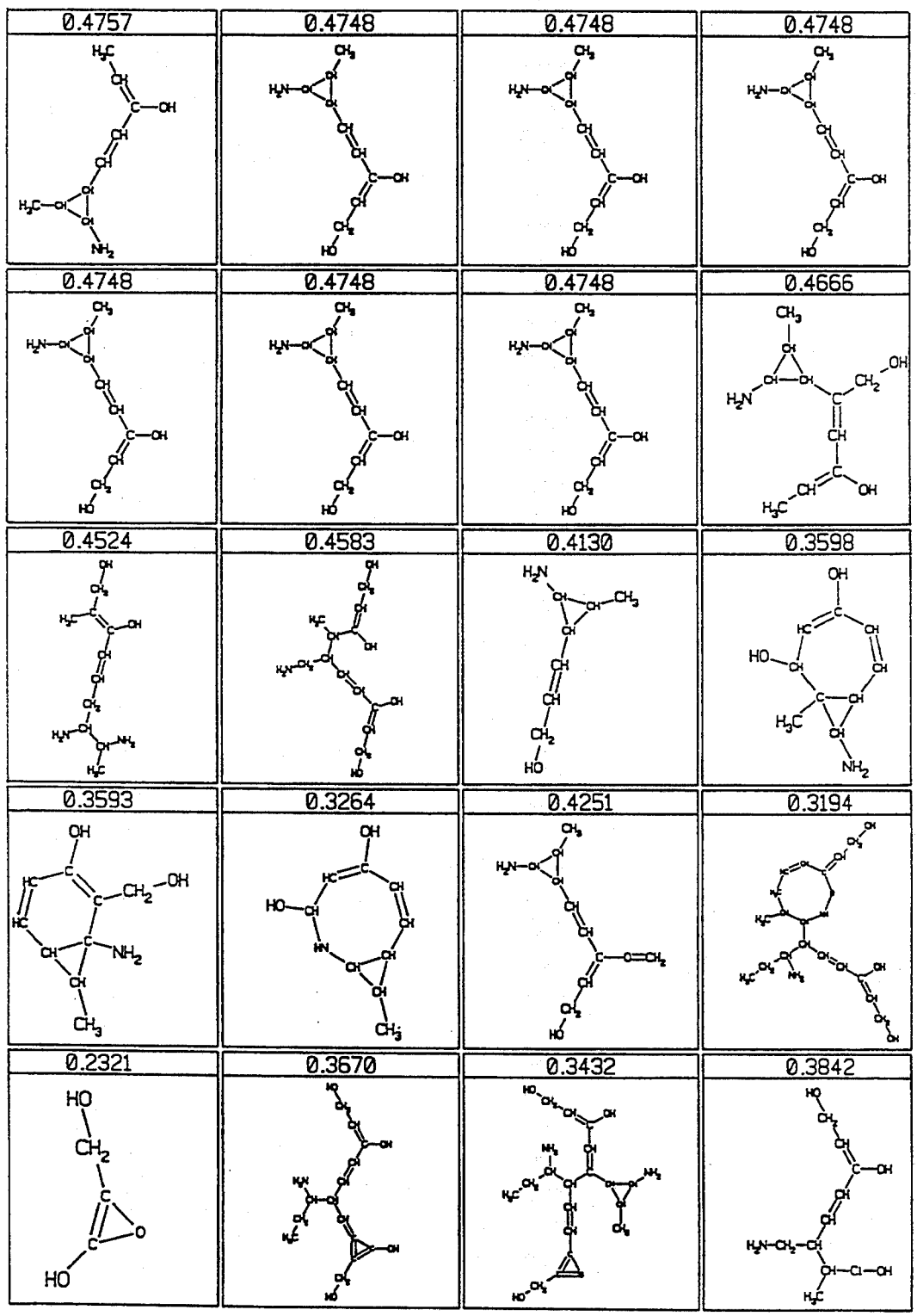
FIGS. 9A-N are respectively the initial population, the 1st, 2nd, 3rd, 4th, 10th, 20th, 30th, 33rd, 34th, 35th, 36th, 37th and 40th generations selected from a sequence of generations, which evolved by the method of FIG. 1 and the similarity-based molecule fitness function of FIG. 3A, where the target module was dopamine and each figure shows chemical diagrams of the molecules comprising a single generation.
Figure 9H:
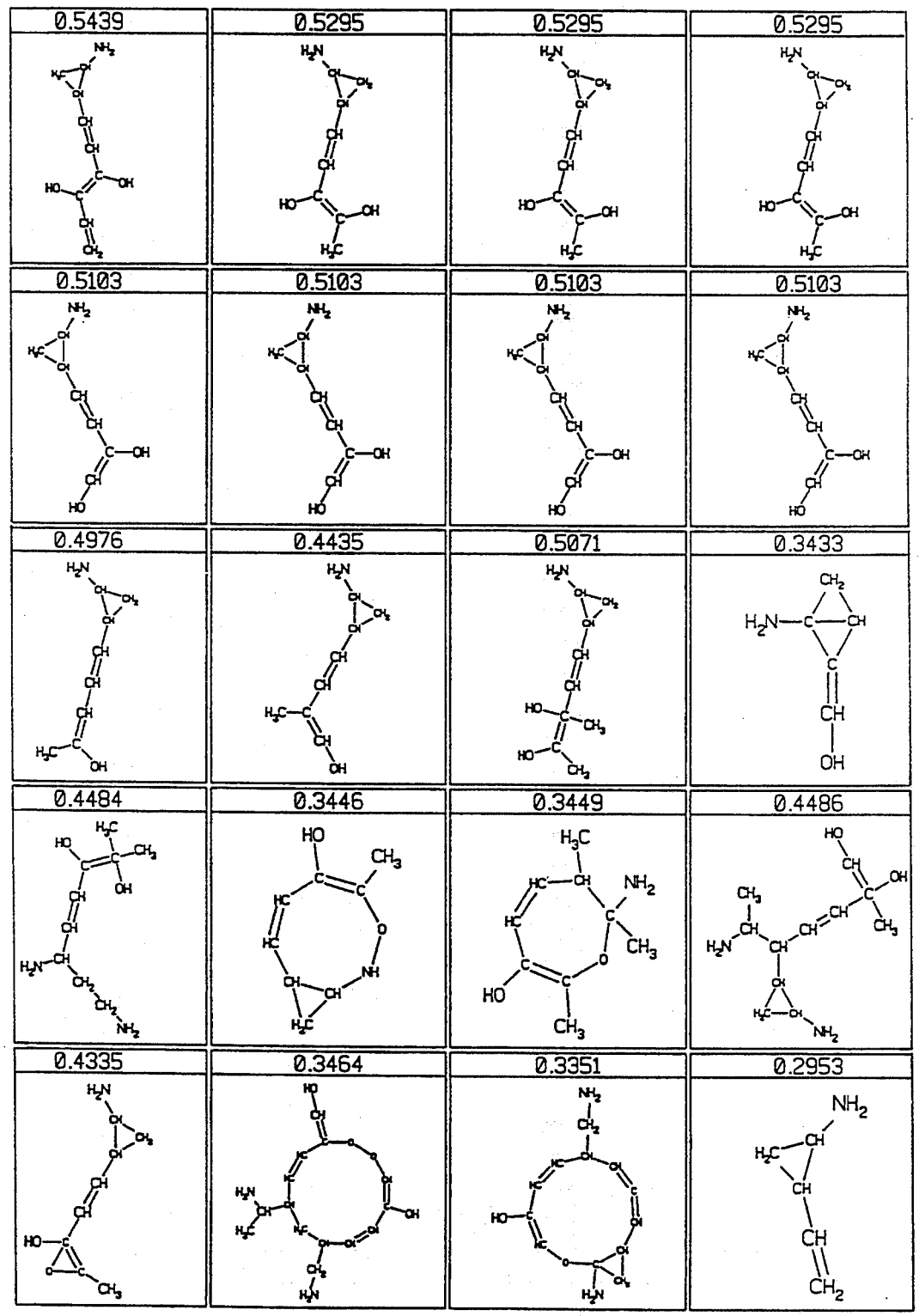
Figure 9I:
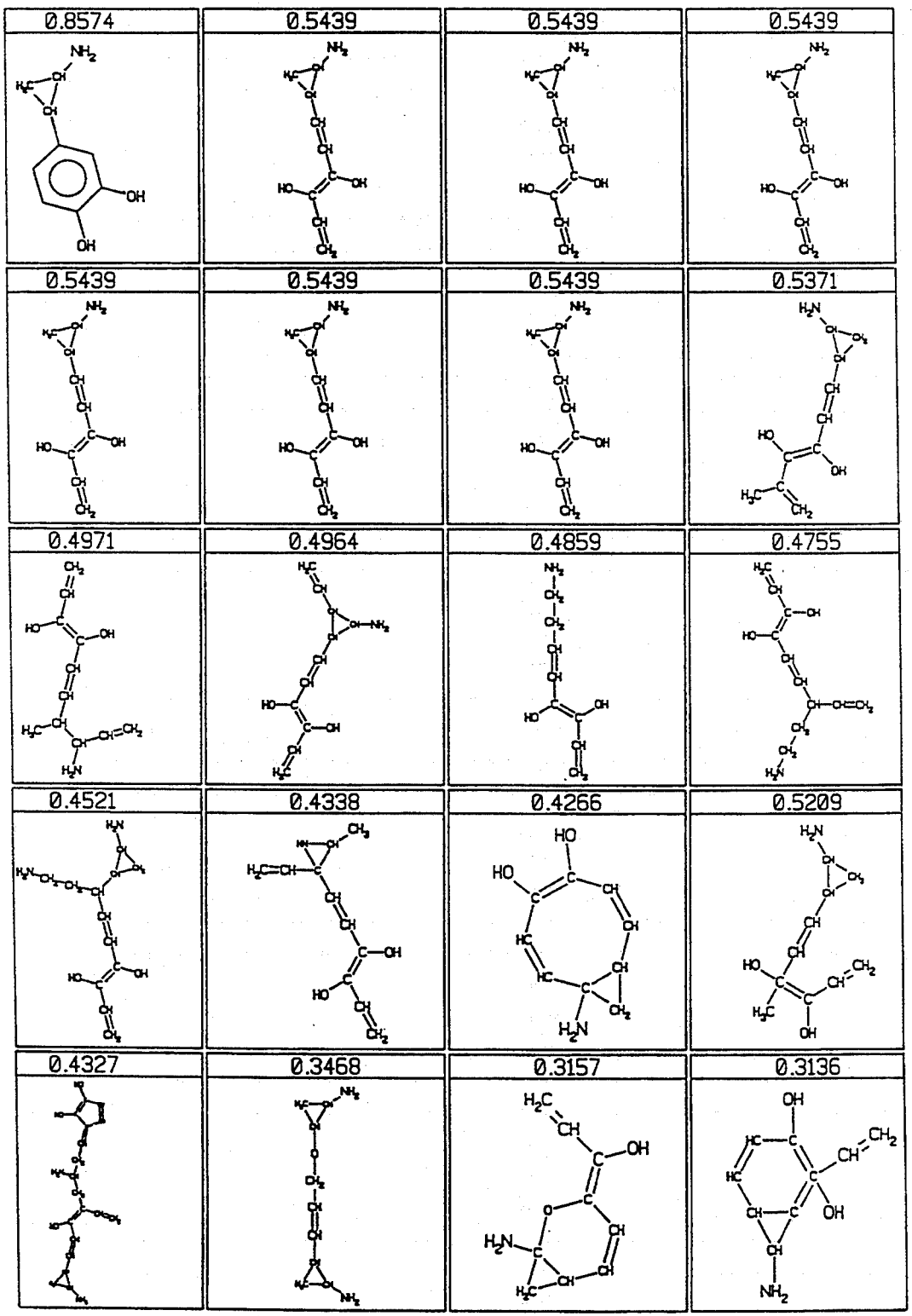
Figure 9J:
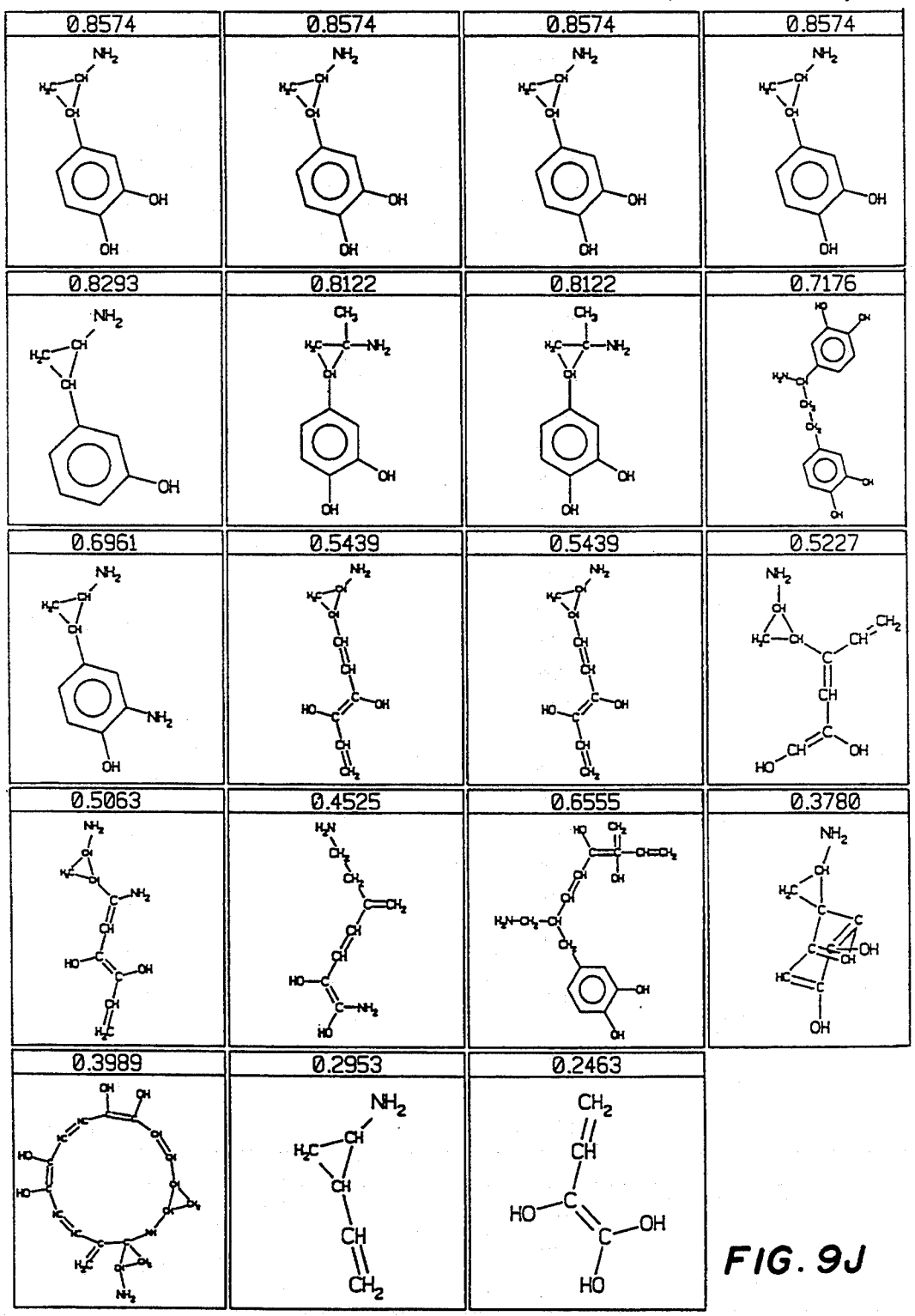
Figure 9K:
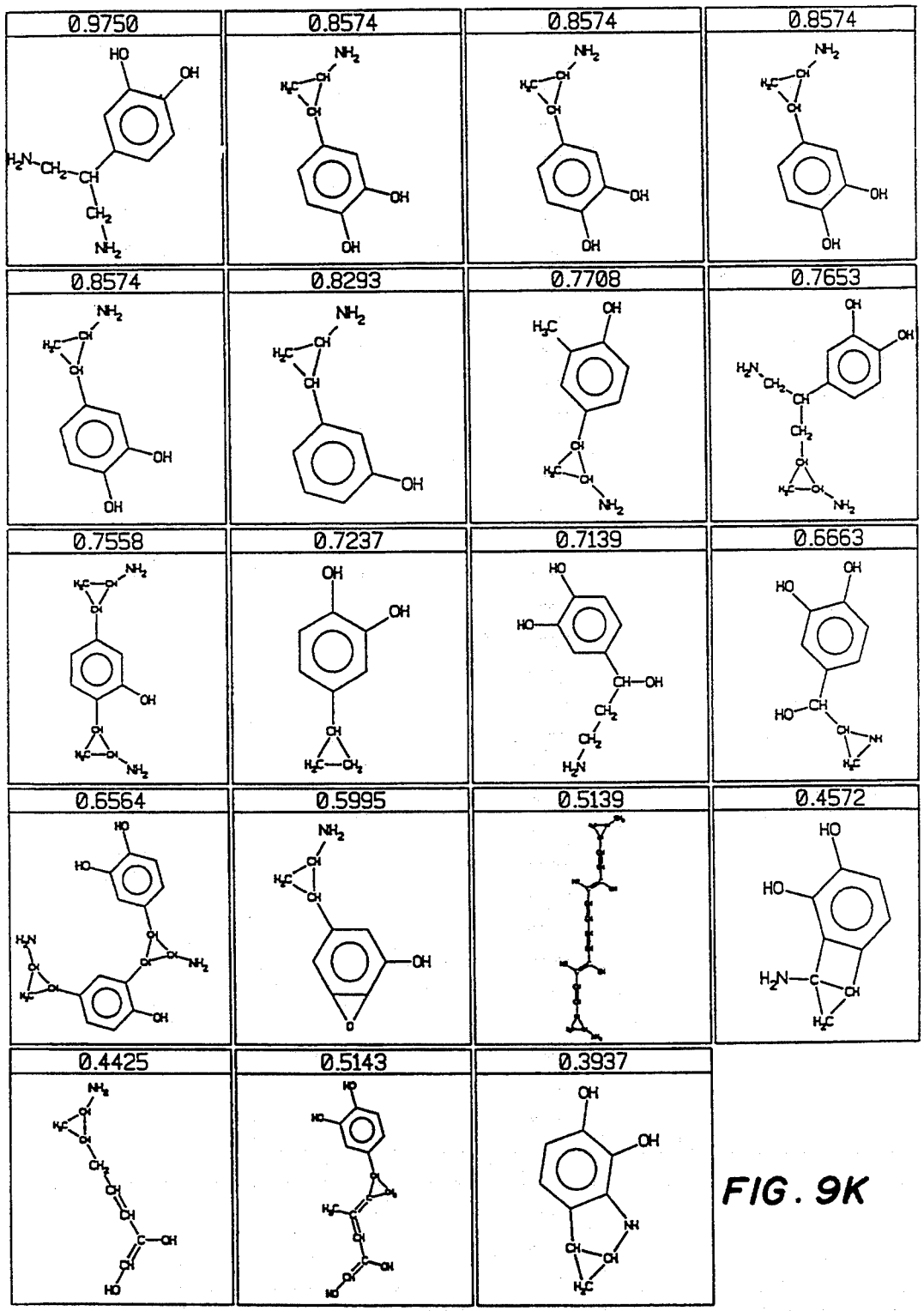
Figure 9N:
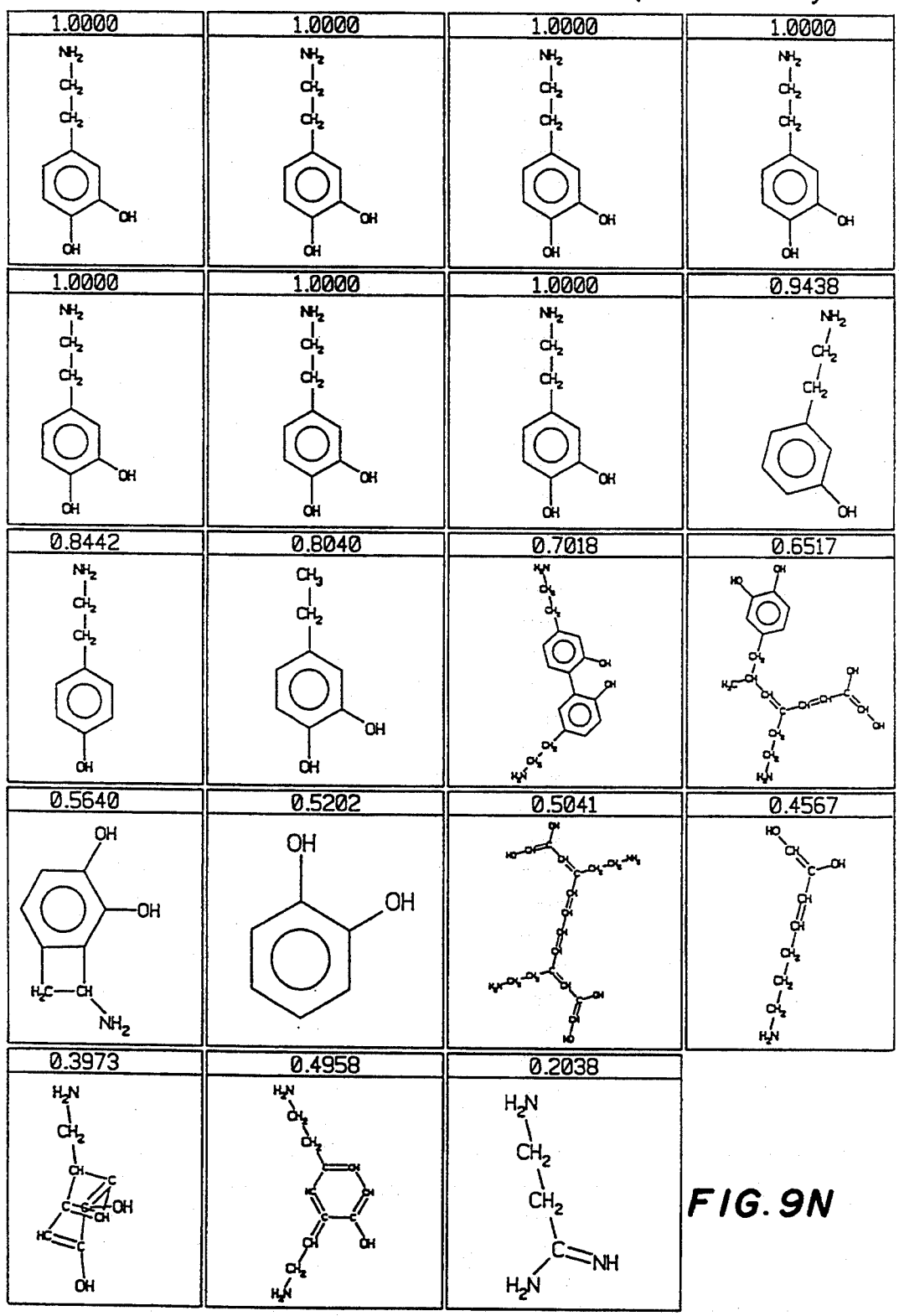

Referring now to the drawings and, in particular, to FIG. 1, there is disclosed a program 10 for carrying out a method of evolving successive generations of molecules using a genetic algorithm. In this invention, each "genome" or member of a population or generation is a molecular structure. Selected generations of such an evolution are shown in FIGS. 9A-N. Each FIG. 9 shows a generation or population of molecular structures; in this illustrative embodiment of the invention, each generation comprises 20 molecular structures, though this number may be varied in other embodiments. Each generation of molecular structures is compared, one structure at a time, with a desired set of physical or theoretical properties to derive an indication or signal which is a measure of the degree of fitness of that structure, i.e., how well that structure matches the desired properties. The method of this invention will continue to evolve generations until a molecular structure of properties sufficiently close to the set of desired properties is evolved as indicated by its numerical score. In particular, the program of FIG. 1 will continue to loop, each loop corresponding to one generation, until the molecular structure with the desired properties evolves.

In FIG. 1, the method 10 starts with step 12, which randomly generates an initial set or population $30_0$. In FIGS. 9, the subscript indicates the number of generations or times that the method 10 has been executed prior to evolving a particular population or generation of molecular structures. FIG. 9A shows an illustrative initial set or population $30_0$ of molecular structures. Initially, the program 10 moves to step 16, which evaluates each molecular structure of the present population or generation with the set of desired physical or theoretical properties. This evaluation uses, as will be explained, any one or more of a potential number of fitness functions. The primary requirement of a fitness function useful for molecular evolution is to compare each molecular structure to a given set of properties and to provide a numerical score as a measure of the degree of fitness of the molecular structure to the set of properties. The remaining steps of the evolving method 10 can readily operate on such a numerical score. Further, if each selected fitness function provides a numerical score, a plurality of fitness functions may be selected to evaluate each molecular structure of a population. The numerical scores of the different fitness functions are merely added together and the composite score is used by the following steps of FIG. 1. As will be explained further below, the use of plural fitness functions permits the evolution of the object molecule toward a corresponding plurality of sets of properties. A desirable property of a fitness function used for molecular discovery is that it is "single-valued". A single-valued function always produces the same result for a given input, i.e., the fitness value is only dependent on the structure of the molecule itself, and not on the evolution history or population composition. The advantage of using single-valued functions is that only unique molecules need to be evaluated for fitness, and those only once. This implementation is optimized for single-valued functions; the fitness of a particular molecule is evaluated at most once.

The chosen fitness functions are evaluated externally in step 18 to allow an extremely high degree of flexibility in the use of this invention. First, the computer language, which is implemented in the following steps 20, 24 and 26, is usually different from that used to carry out the fitness function in step 18. As will be elaborated upon below, the operations carried out by these different steps require different computer languages and, in particular, the molecular structures are represented by different models which require different languages. For example, the subprocess 18c described below with respect to FIG. 3C requires that the molecular structures be represented in a pharmacophore description, whereas the steps 20, 24 and 28 are expressed in terms of molecular graphs. The evolving steps 16, 20, 24 and 28 are independent of a particular fitness function which may be implemented in step 18 and, in fact, may be used with different fitness functions or even a plurality of fitness functions without changing the particular implementation, e.g., the computer language, in which these steps are expressed. Second, the independence of step 18 from the remaining steps of the evolving method 10 increases the flexibility of the computer architecture used. For example, a first computer may be used to execute steps 16, 20, 24 and 26, while a different computer or set of computers may be used to execute step 18. Where the employed fitness function is particularly complex, a separate computer may be used for each member or molecular structure of a population, whereby a plurality of computers may be run in parallel. As will be explained below with respect to FIG. 3F, the comparison steps are not necessarily carried out theoretically by a computer, but rather the molecular structures may be actually made or synthesized, and their fitness measured.

The program 10 moves to step 22, which evaluates each molecular structure of the current generation as to whether that chemical structure is viable. Step 22 determines the degree to which a proposed structure can exist or is stable in the real world. Step 22, like step 18, produces a numerical score indicative of the viability of the evaluated molecular structure. The fitness score produced in step 18 is added to the viability score produced in step 22, to produce a composite score for each molecular structure of the current generation. The composite scores for each molecular structure of the current generation and an "elite" history comprised of those molecular structures with the highest scores are saved in memory in step 24. Next, the molecular structures and composite scores are displayed upon a CRT in step 26. Such display resembles one of the FIGS. 9, i.e., the molecular structures of a single generation plus the composite score for each molecular structure. Next, step 28 applies the genetic algorithm to generate the next generation of molecular structures. As in nature, the molecular structures which most closely resemble the set of desired properties as indicated by the composite scores are favored in the next generation. As will be explained below with respect to FIGS. 5–8, selected ones of the higher scoring molecules are "cloned" into the next generation or selected parts of their structures are "bred" with each other to form the molecular structures of the next generation. The "next generation" then becomes the "current generation or the present population" (indicated by the arrow between the data objects 30 and 14), and the method 10 is repeated to evolve the next generation of molecules. The method continues to be repeated and corresponding generations of molecules are generated until a molecular structure with a sufficiently high composite score is obtained to predict the strong likelihood that the evolved molecular structure will exhibit the set of desired properties.

To use a computer to work on a molecule, e.g., to carry out the method 10 of evolving successive generations of molecules as described above with respect to FIG. 1, it is necessary to represent the molecules and their structures in a suitable form of digital encoding. There are two different types of such digital encoding, which are used to carry out selected of the steps of method 10 dependent upon the adaptability of a particular encoding to be processed by certain steps of the program 10. The first type of encoding, known as molecular graph encoding is well-suited for manipulating molecular structures, e.g., the molecular reproduction with mutation and crossover as carried out in step 28, but is poorly-suited for communicating molecular populations between programs, e.g., performing the fitness evaluation of steps 16 and 18, because it is highly dependent on specifics of the data representation. Molecular graph encoding is further described in the following: 1) *Chemical Structures* 2, edited by Wendy A. Warr, "GEMINI, a Generalized Connection Table Language and Interpreter" by D. Wieninger and A. Weininger, published by Springer Verlag, ISBN 3-540-56369-5 (1993), and 2) *Chemical Information Systems, Beyond the Structure Diagrams*, by D. Bawden and E. M. Mitchell, published by Ellis Horwood (London), ISBN 0-13-126582-2 (1990). A second type of molecular encoding takes a lexical form, wherein a molecular object is represented as a linear notation, i.e., a sequence of printable characters, which is known as SMILES (Simplified Molecular Input Line Entry System), which is described in "SMILES, a chemical language and information system. I. Introduction to methodology and encoding rules", D Weininger, *J. Chem. Info. Sci.*, 28, 31 (1988). In this embodiment of the molecular genetic algorithm, SMILES is used for communication and storage of molecular populations. SMILES is more suitable than internal graph encoding methods for purposes of communication and storage of molecular populations because it consists only of textual characters and thus provides a compact and machine-independent representation of molecules.

In this embodiment, the digital representation of a molecular graph represents an internal "molecule object". SMILES is the lexical form of a molecule object. Conversion of molecules encoded in the SMILES language to internal form is known as "SMILES interpretation" and is carried out in most of the fitness functions described herein, e.g., subprocesses 94, 112, 132, etc. Conversion of the internal form to SMILES is known as "SMILES generation" and is done whenever external structures must be communicated to an external process or storage. For example, in steps 16 and 24, the molecular structures are "translated" into SMILES before being communicated respectively to steps 18 and 26.

The use of the rigorously defined SMILES language for communication of molecular populations allows a single embodiment of the molecular genetic algorithm to operate with any one or more of a variety of external fitness functions, without any changes in implementation of the genetic algorithm and, in particular, steps 16, 20, 24 and 28.

Molecular graph encoding, referred to above as the first type of encoding, may be used to represent a molecular structure internally, i.e., in steps 16, 20, 24 and 28, as a molecular graph. The molecular graph is a collection of nodes connected by edges. A labeled graph is a graph which has its nodes and edges labeled in some way which makes them non-equivalent. The molecular graph is a labeled graph in which nodes represent atoms (node labels include atomic properties such as atomic number and charge) and edges represent bonds (bond labels include bond order and type). The molecular graph therefore represents a valence model of a molecule. Molecular graphs are typically displayed as diagrams as illustratively shown in FIGS. 9 with node labels shown as character strings, e.g., "CH2" and bonds shown as single, double, or triple, lines connecting atoms. Molecular graphs are not limited to representing nodes as atoms. Nodes can represent fixed collections of atoms, e.g., amino acid residues in polypeptides. But in all cases, nodes in molecular graphs represent "atomic" or indivisible units with respect to molecular representation.

The second type of encoding known as SMILES provides a method for external representation of molecules for communication between program units and for output of results. Evaluation of molecular fitness is carried out in steps 16 and 18 on molecules digitally represented in the SMILES language. A brief description of relevant aspects of SMILES appears below. SMILES is a linear notation for molecules consisting of a series of characters not including spaces. These characters are put together in accordance with five basic rules which are described below.

Rule 1 requires that atoms be represented by atomic symbols inside brackets, e.g., the string "[Pb]" represents elemental lead. Charges or unusual hydrogen attachments must be represented inside brackets, e.g., "[OH3+]" represents the hydronium ion. The elements B, C, N, O, P, S, F, Cl, Br and I may be written without brackets when they occur at their lowest normal valence consistent with explicit bonds, e.g., "C" represents methane. Symbols beginning with a lower case letter represent aromatic (sp2) atoms.

Rule 2 requires that bonds be represented by the symbols "—" (single), "=" (double), "#" (triple), and ":" (aromatic), e.g., "C=O" represents formaldehyde. Atomic symbols appearing adjacent to each other are assumed to be connected by a single or aromatic bond, e.g., "CO" represents methanol.

Rule 3 requires that branches be indicated by enclosing the branched group in parentheses, e.g., "CC(=O)O" represents acetic acid. Branches can be nested or stacked as desired, e.g., "ClC(Cl)(Cl)Cl" represents carbon tetrachloride.

Rule 4 provides that ring closures are indicated by pairs of matching digits representing extra bonds, e.g., "CCCCCC" represents hexane, "C2CCCCC2" represents cyclohexane, and "c1ccccc1" represents benzene.

Rule 5 specifies that portions of a molecule, which are not joined by formal bonds, be separated by a period (nonbond), e.g., "[Na+].[O—]c1ccccc1" represents sodium phenoxide.

The basic SMILES rules above are adequate to describe the vast majority of organic molecules, and are adequate for the purposes of this discussion. The most important property of SMILES is that a molecule may be unambiguously represented by a string of characters.

To evolve unbiased successive generations of molecules, it is useful to start with a collection of random molecules, called a random population. Random starting populations generally produce superior results than collections of molecules having properties similar to those desired because there is less built-in bias towards one particular class of answer. Method 10 has been carried out by selecting molecular structures with characteristics or properties similar to those of the desired set for inclusion in the initial generation of molecular structures. If similar molecular structures are included, the evolved structures are biased towards the class of similar molecules. On the other hand, if molecular structures are randomly generated, the evolving method 10 will generate unique structures which not only tightly fit the desired properties and would not be generated had an initial population of molecules with desired properties been selected. In general, the selection of a random initial population of molecules will evolve a greater variety of object molecules, than if the initial population had been selected with the desired properties. As will be explained below, the randomly generated molecular structures of the initial population need not be existing molecules or even be viable in the real world. Generating a random population may be carried out by using either internal or external representations as respectively shown in FIGS. 2A and B.

Figure 2A:
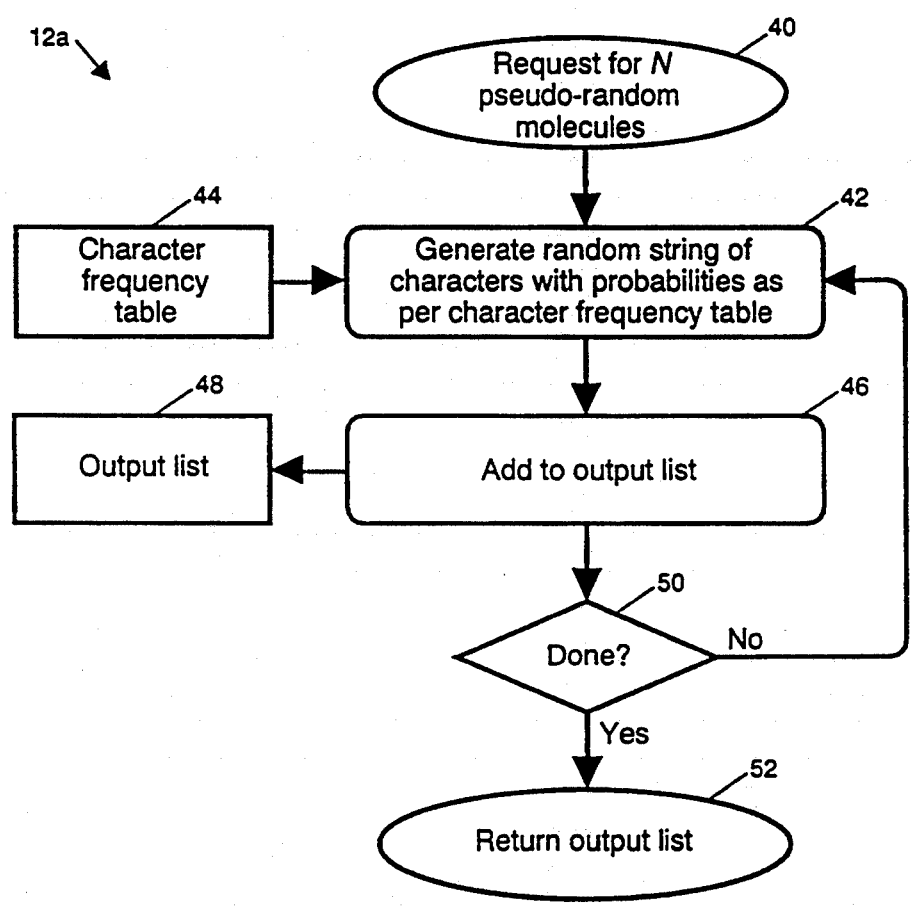
FIGS. 2A and B are more detailed, low level flow diagrams of alternative methods of generating an initial population of molecules as generally indicated by step 12 of the high level flow diagram of FIG. 1, by respectively producing random character strings in a linear notation and producing a randomized graph from nodes and edges obtained from a primitive frequency table.

Referring now to FIG. 2A, there is shown an expanded subprocess 12a of randomly generating an initial population of molecules using the external representation known as SMILES. The advantages of using the SMILES type of encoding are speed and simplicity. A potential disadvantage is that many linear strings of characters will not represent valid, viable molecules. First, step 40 requests a given number N of molecules. Next, step 42 expresses a single molecule in the SMILES language at a time by selecting pseudo-random characters in accordance with the priorities or bias stored in a character frequency table 44. The character frequency table 44 is constructed by loading therein each chemical found in the periodic table at a frequency corresponding to the occurrence of a particular chemical in nature. Each molecular structure is separated from the adjacent structures by blanks. The resultant table 44 illustratively includes 50,000 chemicals and approximately 1,000,000 characters and blanks. In particular, step 42 randomly picks one character at a time from the table 44. Characters are continued to be picked until a blank is picked. The picking of a blank defines the end of one molecule. Thus, the characters and the length of each molecule is randomly determined. When one molecule is completed, the next is begun. Such bias is driven by a table of character frequencies found in databases of known molecules. For example, when working with organic molecules, the letter "C" representing carbon appears very frequently, i.e., 69% of the time, "N" appears frequently, i.e., 11% of the time, while the letter "Z" never appears. The use of the character frequency table enhances the probability that viable molecules will be evolved. When step 46 senses the occurrence of a blank, that string of characters is output to a list 48. Step 50 determines whether a whole population of molecules, N molecules, has been generated. If not, the subprocess 12a loops back to step 42; the subprocess 12a will continue to loop through steps 42, 46 and 50 until a whole population of N molecules is generated. When complete as determined by step 50, a return to the step 14 of the method 10 of evolving is made. It is appreciated that the randomly generated strings of characters may not often represent viable molecules. Even so, experience shows that after 30 or 40 reiterations of the evolving method 10 invalid molecules will disappear from the following generations and only valid molecules will be left.

Figure 2B:
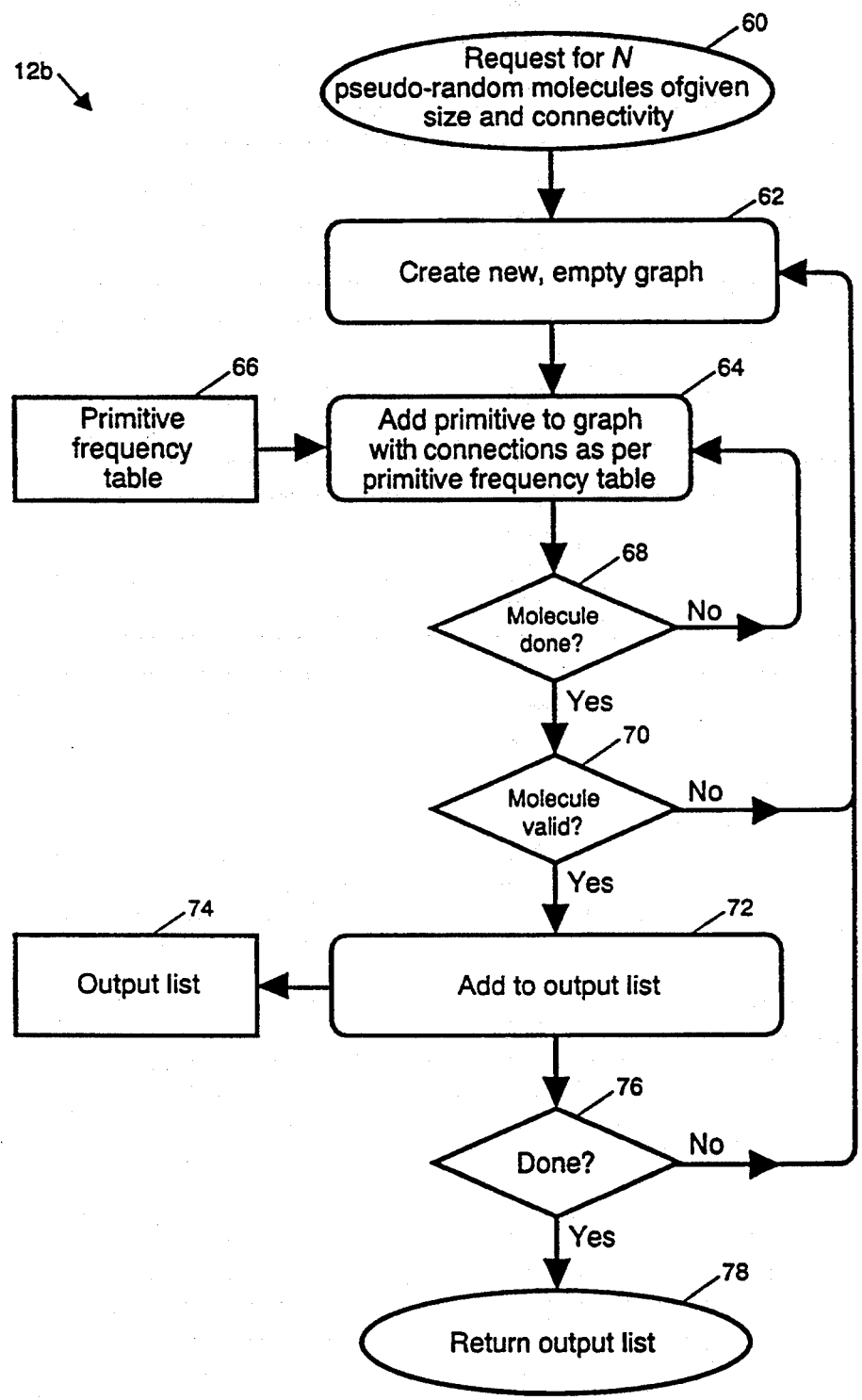

Referring to FIG. 2B, there is shown a preferred, more powerful step or subprocess 12b of generating a random population of molecules using molecular graphs as internal representations. An advantage of the subprocess 12b is that molecular graphs can be easily constrained to represent valid molecules. Evolving generations of molecules by method 10 from an initial population randomly generated by subprocess 12a indicated a bias based on the use of the SMILES language, against branches and ring structures. Subprocess 12b, which expresses molecular structures as graphs, did not exhibit such a bias against branch and ring structures. A disadvantage of subprocess 12b is that it is more complex and time-consuming than the SMILES based subprocess 12a of FIG. 2A. After receiving a request for the initial population of N molecules in step 60, step 62 creates for each molecule an empty molecular graph containing no atoms or bonds. Then, step 64 psuedorandomly adds from a table of "graph primitives" 66 in the form of atoms and bonds between atoms, to the molecular graph. The "primitives" are the simplest, basic components of the molecular structure to be evolved, and would include the nodes or atoms and the edges or bonds. The table 66 is constructed with a frequency tabulated in accordance with their appearance of particular nodes or edges in nature or as desired to produce a molecule of desired properties. For example, the probability in nature of finding a double bond between O and C is relatively high, i.e., 23% of the time, whereas the probability of selecting a double bond between F and anything is zero. In an illustrative embodiment of this invention, "primitives" could be selected for the table 66 from the "Pomona College Medicinal Chemistry Data Base", by Albert Leo, Pomona College, Claremont, Calif. Of course, other databases of molecules could be used to construct the table 66.

Step 68 determines whether the graph of the molecule under construction is complete. In step 68, parameters are set indicative of the minimum and maximum number of atoms, e.g., 2 and 20, as well as the connectivity or number of bonds per atom, e.g. 1.2. For each molecule to be generated, step 68 selects randomly the number of atoms between the set minimum and maximum numbers and determines whether the molecular graph has the required number of atoms and bonds. If not, the subprocess 12b continues to loop through steps 64, 66 and 68 until the molecular graph is complete. After step 68 determines that the molecular graph is complete, step 70 determines whether the generated molecule is valid. Step 70 determines molecular validity in terms of whether the protons, electrons and charges of the constructed molecule satisfy the laws of chemistry and does not evaluate molecular stability nor reasonableness as done in step 22 of FIGS. 1 and 4. If not a valid molecule, the subprocess 12b discards the invalid molecule and returns to step 62 to create a new molecular graph. If the molecule is valid as determined in step 70, step 72 adds the valid molecular graph to an output list 74. Next, step 76 determines whether N molecules have been randomly generated and, if not, the subprocess 12b continues to loop through steps 62–76 until an entire population of N molecules is generated. When the entire population has been generated, the output list 74 is returned to the method 10 of evolving and, in particular, to step 16 of FIG. 1. The subprocess 12b, which uses molecular graphs, has proved to be more efficient than subprocess 12a, which operates on linear strings of characters. Subprocess 12b was used to generate the molecular structures shown in FIGS. 9A–N, 12A and B, and 13A and B.

After an initial population of N molecules has been randomly generated in step 12 or the next generation of N molecules has been evolved in step 28, the method 10 of evolving moves as shown in FIG. 1 to step 18, which evaluates each "genome" or molecule of the population or generation with a fitness function. The object of the method 10 of molecular evolution is to produce molecular structures, which optimize a given objective function. In evolutionary terms, such functions are known as "fitness functions". The primary requirement of a fitness function useful for molecular evolution is that it produces a numerical measure of how well the object molecular or structure exhibits the set of desired and/or theoretical properties. Illustrative examples of fitness functions are discussed below with respect to FIGS. 3A, B, C, D, E, F and G to demonstrate the types of functions, which are suitable for use with the evolving method 10 of this invention.

As shown in FIG. 1, method 10 provides a simple interface to the external fitness function step 18, i.e., the fitness function is a subprocess implemented by a computer program running independently from the molecular evolution program. At each generation, the population is written out as a list of SMILES strings, e.g., a population of five small molecules might be:

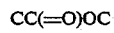

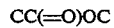

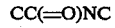

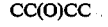

The fitness function step 18 operates by evaluating the fitness of each molecule as a numerical value and associating that value with the SMILES, e.g.

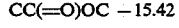

Since the molecular genetic algorithm carried out by step 28 is a minimizer, molecules with lower numerical scores are considered better than those with higher scores. This naturally corresponds to fitness functions such as the binding fitness function to be described below with respect to FIG. 3D, where the results are in kcal/mol with more negative numbers indicating tighter binding. An adjustable parameter, i.e., a "fitness factor", is provided which allows the fitness values to be converted to scores in an arbitrary manner, i.e., if the fitness factor is negative, higher values lead to lower scores and are considered "better".

Figure 3A:
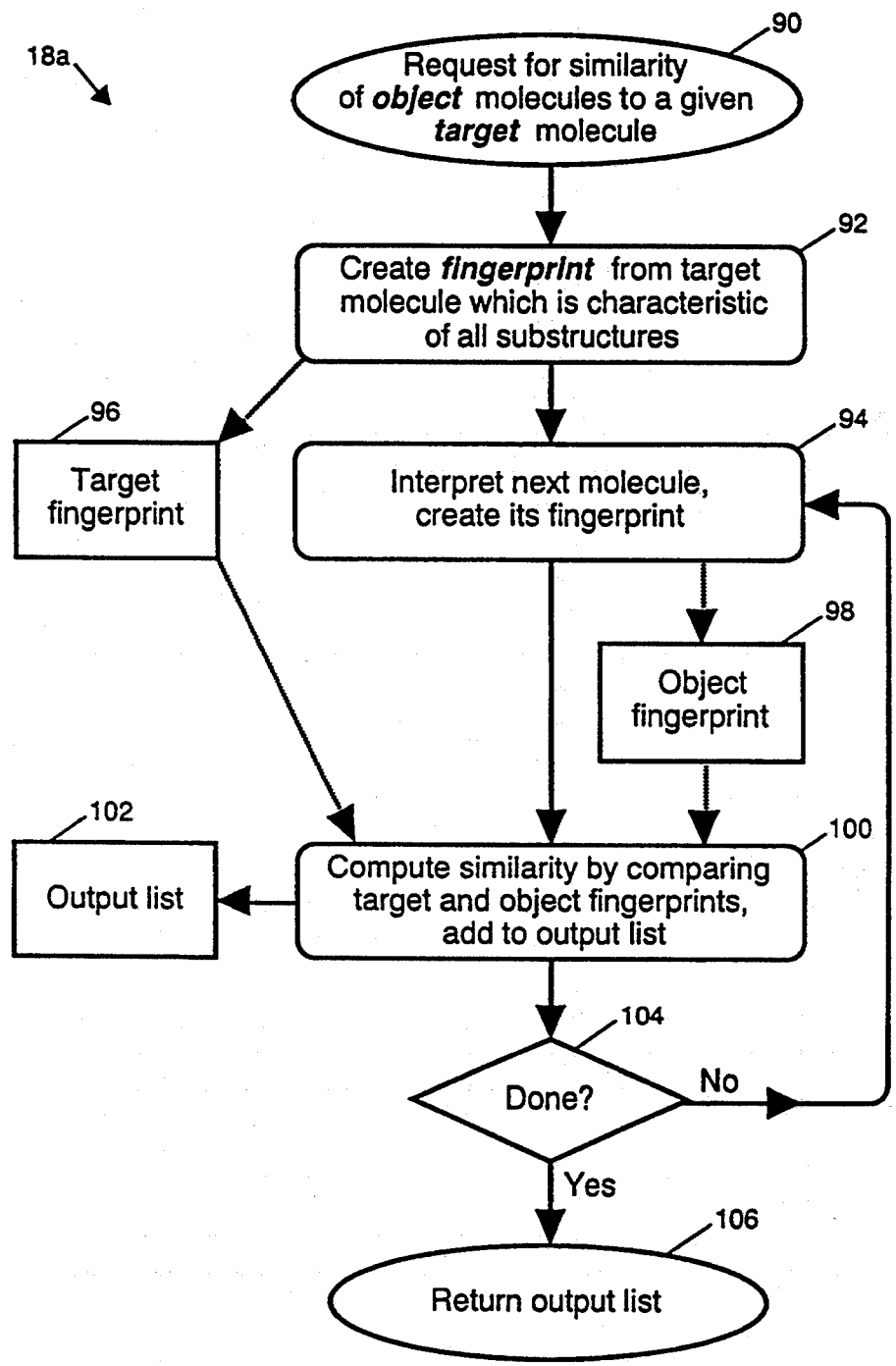
FIGS. 3A, B, C, D, E, F and G are more detailed, low level flow diagrams of alternative methods of evaluating each molecule of a given population as generally indicated by step 18 of the high level flow diagram of FIG. 1, by respectively using a fitness function which (A) compares the similarity of a bitwise representation of each molecule, i.e., an object molecule, with a target molecule, which (B) compares the similarity of the bitwise representation of each object molecule with a class of target molecules, which (C) compares the fit of the molecules to a given geometric pharmacophore model, which (D) computes a theoretical binding energy between the object molecule in the form of the drug to be designed and a molecular model of a protein or enzyme, which (E) evaluates the fit of each molecules with a derived model of a molecular field, which (F) uses measured values of binding of a synthesized drug upon an actual sample of the protein or enzyme, and which (G) allows multiple fitness functions to be combined to form a composite fitness function.

Referring now to FIG. 3A, there is shown a relatively simple step or subprocess 18a for carrying out a fitness function, which determines the similarity of each molecular structure in a population, i.e., an "object" molecule, with the molecular structure of a given or "target" molecule. The subprocess 18a for carrying out the molecular-similarity-based fitness function was run for an illustrative "target" molecule of dopamine, whose molecular structure is shown in the upper left hand corner of FIG. 9L to evolve the sequence of generations shown in FIGS. 9A–N. The subprocess 18a begins in step 90, which receives the molecular-similarity-based fitness function request and identifies the given or "target" molecule. Next, step 92 encodes each substructure of the "target" molecule, e.g., dopamine, up to a certain size, e.g., 8 atoms, as a data object in the form of a bit string which is known as a target "fingerprint" 96. A description of a "fingerprint" and how one is used to compare molecular structures is described in *Clustering in Chemical Information Systems*, by Peter Willett, Research Studio Press, Wile, N.Y., 1987. Step 94 also generates an "object fingerprint" 98 of each "object" molecule of the present generation. Step 100 determines the similarity between the "object fingerprint" 98 and the "target fingerprint" 96 in terms of the distance or similarity metric. The similarity metric used here is the following binary Tanimoto metric applied to a bitwise representation of molecular substructures:

$$T(t,o) = \frac{N_c}{N_t + N_o - N_c}$$

where $T(t,o)$ is the Tanimoto similarity of molecules t and o $N_t$ is the number of substructures in target molecule t $N_o$ is the number of substructures in object molecule o $N_c$ is the number of substructures common to molecules t and o Step 100 outputs a value of the metric distance, where 0.0 indicates complete dissimilarity and 1.0 indicates complete similarity. For use with the step 28 of evolving generations with the genetic algorithm which has a minimizing objective, the Tanimoto similarity is multiplied by a "fitness factor" of $-10.0$ to produce a score for which smaller (more negative) numbers correspond to better fitness. The distances for the generations of molecules produced by the subprocess 18a of the similarity-based fitness function are shown in FIGS. 9A–N for each molecular structure of each generation. For example, the most similar molecular structure of the first generation as shown in the upper left-hand corner of FIG. 9B has a metric distance of only 0.1889, which indicates that such a molecular structure is relatively dissimilar from the "target" molecule, dopamine. After the metric distance is calculated, step 100 places it in an output list 102. Next step 104 determines whether all N of the molecular structures of the generation have been compared to the "target fingerprint" 96 and, if not, the subprocess 18a continues to loop through steps 92, 94, 100 and 104. Thus, it is necessary to calculate only once in step 94 the "fingerprint" 96 of the "target" molecule, which is then repeatedly compared with each "object fingerprint" 98 of a generation in step 100. After the metric distance is calculated for each molecule of the generation, the output list 102 is returned in step 106 to the recording step 24 of the evolving method 10 of FIG. 1.

The subprocess 18a of the similarity-based fitness function in effect evolves the "object" molecules toward a known or target molecule. While of limited value to evolve new molecular structures, this subprocess 18a demonstrates clearly the efficacy of the genetic algorithm to evolve a succession of generations of molecules with higher and higher metric distances, thus indicating that evolved molecular structures proceed toward the given objective. FIGS. 9A–9N show the population at generations 0, 1, 2, 3, 4, 10, 20, 30, 33, 34, 35, 36, 37 and 40, respectively. The target molecule was dopamine, which appears in the upper left hand corner of FIGS. 9L, 9M, and 9N (generations 36, 37, and 40). Each figure represents the entire population, with molecules of a population sorted by score, and fitness values in terms of the metric distances. To understand the fitness values, note that aromatic rings (rings with circles drawn inside them) are chemically equivalent to rings with alternating single and double bonds. In this example, the initial population as shown in FIG. 9A consisted exclusively of single-bonded molecules with two heavy atoms, such as methanol and ethane. The effect of reproducing this population can be seen in the first generation of FIG. 9B. There, molecules appear with three heavy atoms, double bonds, e.g., ethene, and also some simpler molecules, e.g., water and ammonia. Since most of the molecules of the starting population are much simpler than the target molecule, early evolution is characterized by increasing complexity as shown in FIGS. 9B–9E. As evolution progresses through generations 10, 20, and 30 as shown in FIGS. 9F–H, the alternating single-double bond pattern in dopamine is established as well as the relative positions of the substituent groups. The first aromatic ring appears in generation 33 of FIG. 9I and is proliferated in the next generation of FIG. 9J, providing a good example of selection of more fit members. The spurious three-member ring is broken in generation 35 as shown in FIG. 9K, resulting in an elite member which is extremely fit as indicated by its metric distance of 0.975. None-the-less, when dopamine itself first appears in generation 36 of FIG. 9L, it is the result of the mutation of a slightly less fit member (deletion of a carbon atom in a molecule with 0.857 fitness), not the incremental mutation of the elite member. Note that though dopamine proliferates through the population rapidly after it originally appears, the genetic algorithm still maintains a high level of population diversity, see generations 37 and 40 in FIGS. 9M and 9N. This behavior is extremely important for "real" molecular discovery problems, where the optimal solution is not known in advance. In the example of FIGS. 9A–N, the parameters were set to accelerate evolution. It is remarkable that this method was able to find a particular chemical from among all chemicals so quickly using random methods, directed only by selection bias towards fit members.

Figure 3B:
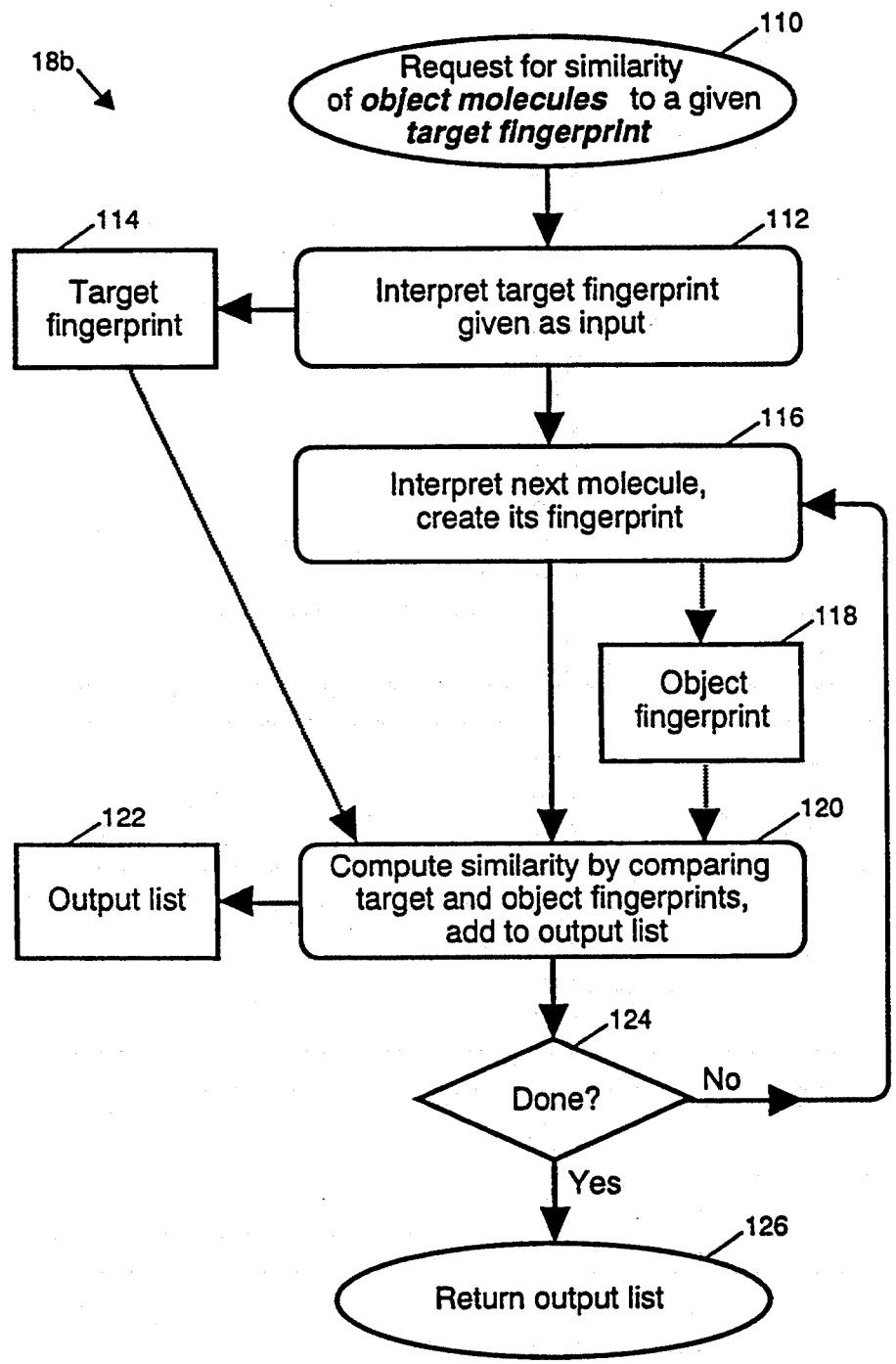

Referring now to FIG. 3B, there is described a step or subprocess 18b which implements a fitness function for determining similarity not to the fingerprint of a single "target" molecule as performed by subprocess 18a, but rather similarity to an arbitrary "target" fingerprint. Thus as the evolving method 10 including subprocess 18b is repeatedly executed, successive generations will evolve new molecular structures which contain structural features described in the arbitrary "target" fingerprint. After step 110 receives the request for molecular fitness function 18b, step 112 interprets and saves the arbitrary "target fingerprint" 114. In a manner similar to subprocess 18a, step 120 compares a "fingerprint" 118 of each "object" molecule to provide fitness scores in terms of similarity metric distances. After each "object" molecule in the population has been compared by step 120, the output list 122 of the fitness scores of the whole population is returned in step 126 to the next, recording step 24 of the evolving method 10.

Subprocess 18b is a modification of the previously-described subprocess 18a and, in fact, is a generalization of the subprocess 18a. Subprocess 18b produces a function which is useful for solving real problems which are not solvable by any other currently available method. The key lies in the selection of the arbitrary "target fingerprint". The fingerprint of a molecule is normally a set of bits which represent structural characteristics of a particular molecule. It is possible to produce a special kind of fingerprint which represents the common structural characteristics of a class of molecules, called a "modal fingerprint". The fingerprints of the molecules of the class are examined, and a bit in the modal fingerprint representing a particular characteristic is set only if more than half of the fingerprints in the class have that bit set, i.e., half of the molecules have that characteristic. The modal fingerprint thus represents only features common to the class and may or may not correspond to the fingerprint of any actual molecule. Using subprocess 18b with such an arbitrary "modal fingerprint" as the target, as the evolving method 10 progresses, new molecules will evolve which have fingerprints which are similar to the "modal fingerprint" and thus are characteristic of the original class, resulting in a method which is of interest for molecular discovery.

Figure 3C:
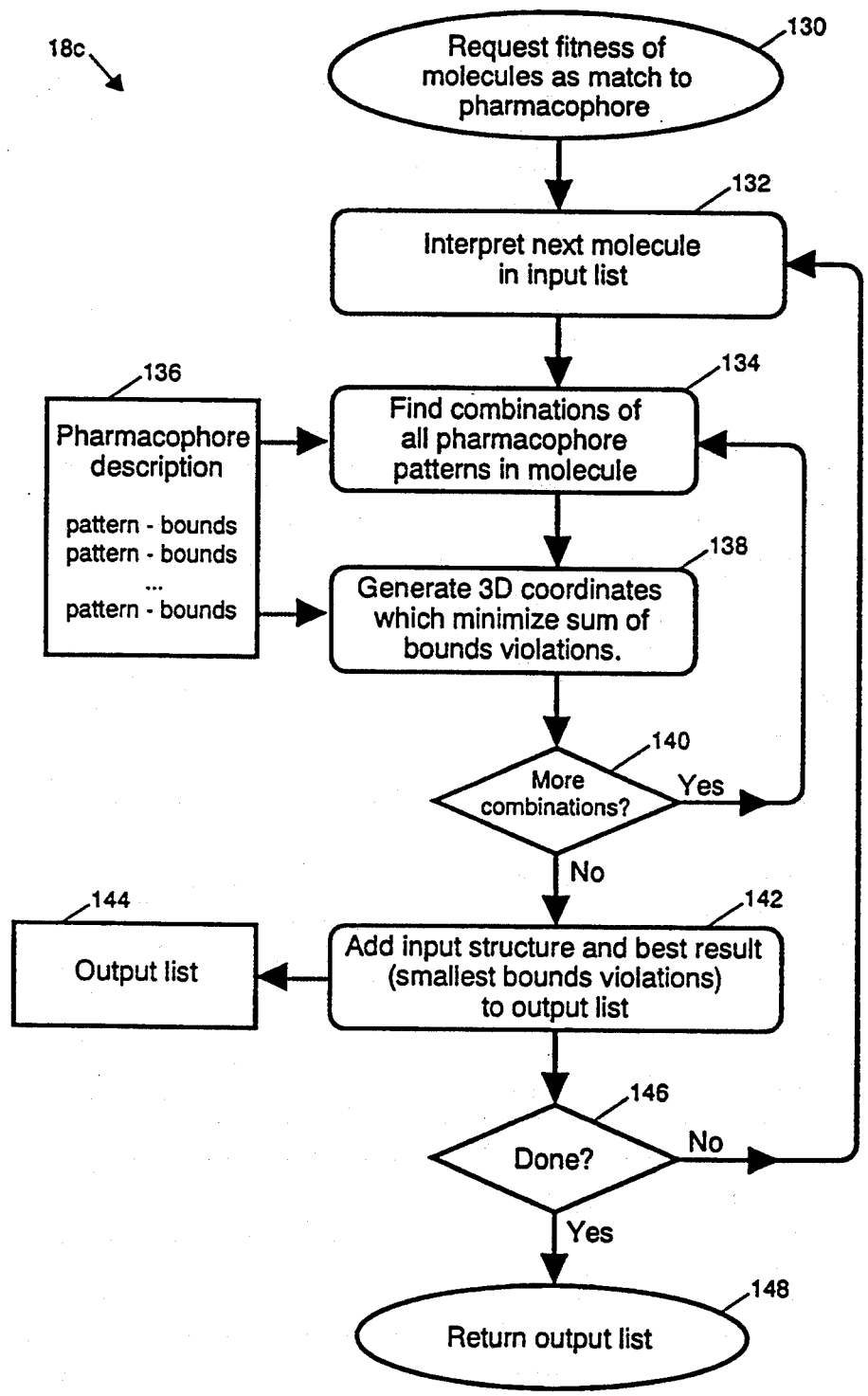

Referring now to FIG. 3C, there is shown the step or subprocess 18c for carrying out a fitness function for computing the fit of a molecule to a geometric pharmacophore model. Pharmacophore models comprise points within a three-dimensional molecular structure and bounds (or limits) on the distances between these points. The molecular structure is typically defined by patterns of atoms in terms of connectivity, i.e., the definitions do not depend on a three-dimensional structure. Such models are derived from conformations of molecules which are known to have a specific pharmacological activity. New molecules which can meet the pharmacophore model constraints are considered to be candidates for drug development. The molecular genetic algorithm, when used with the fitness function described in FIG. 3C, produces new molecules which meet such pharmacophore constraints.

An example of a geometric pharmacophore model for the nicotinic acetylcholine receptor is described in "The Ensemble Approach to Distance Geometry: Application to the Nicotinic pharmacophore", R. P. Sheridan, R. Nilakantan, J. S. Dixon, and R. Venkataraghavan, J. Med. Chem., 29, 899 (1986). Three points were found to be essential to define a pharmacophore model: a cationic center, e.g., an aliphatic nitrogen (A), an electronegative atom, e.g., a pyridine nitrogen or carbonyl oxygen (B), and one or more atoms (C) which form a dipole with B, e.g., an aromatic ring or a carbonyl carbon. The nicotinic pharmacophore model also requires that distances between these points A, B and C; such distances are expressed in angstroms: 4.8 (A–B), 4.0 (A–C), and 1.2 (B–C). Many molecules which can form conformations which fit these criteria are active with respect to the nicotinic receptor, either as agonists or antagonists. This pharmacophore model is an example of the description that comprises the data object 136 in FIG. 3C, i.e., a set of patterns comprising a plurality of points, each for example including atom pairs such as aliphatic nitrogen and pyridine nitrogen, and bounds, which defines the limits between which each distance between 2 connected points may be set, e.g., 4.8 ±0.05 angstroms.

The subprocess 18c starts in step 130 with a request for pharmacophore fitness of a list of molecules of the present population. Step 132 interprets each molecule in turn by converting the communicated SMILES representation of each molecule into a corresponding molecular graph thereof, and then initializes its fitness to a very poor value. Step 134 then identifies the points or atoms in the molecule which correspond to those of the patterns in a pharmacophore model description 136, and loops over all combinations found in the molecule. Using the nicotinic pharmacophore model for example, if a molecule has a combination of two atoms matching pattern A (call them A' and A''), two atoms matching pattern B (B', B'') and one atom matching pattern C (C'), a loop including the steps 134, 138 and 140 would execute 4 times, once for each of the patterns: A'B'C, A'B''C, A''B'C, and A''B''C. For example, during the first execution of the loop, the pharmacophore model would be fitted with atoms A', B', and C as the three geometric points in the model; during the second loop, A'', B', and C would be tried In each loop, conformations are generated which force the specified atoms to be separated by distances required by the pharmacophore model, i.e., the bounds in the pharmacophore description 136. The 3-D conformations are generated by distance geometry in the same manner as described by the above referenced Sheridan et al. publication. Fitness is taken to be the sum of bounds violations with the lowest value being the best fit; such a fitness value is written to an output list 144 by step 142. Step 146 determines whether each of the N molecules in the population has been done, and when all are evaluated, the output list is returned to the recording step 24 of the evolving method 10 as shown in FIG. 1.

The results of operating the molecular genetic algorithm with a pharmacophore fitness function are populations of novel molecules which can conform to 3-D constraints. Note that this is done without having the genetic algorithm process 3-D conformational data; only the external fitness function deals with the 3-D coordinates. Evolving molecules which fit a geometric pharmacophore model is a simple form of evolving molecules in 3-D; more sophisticated examples are discussed below.

Figure 3D:
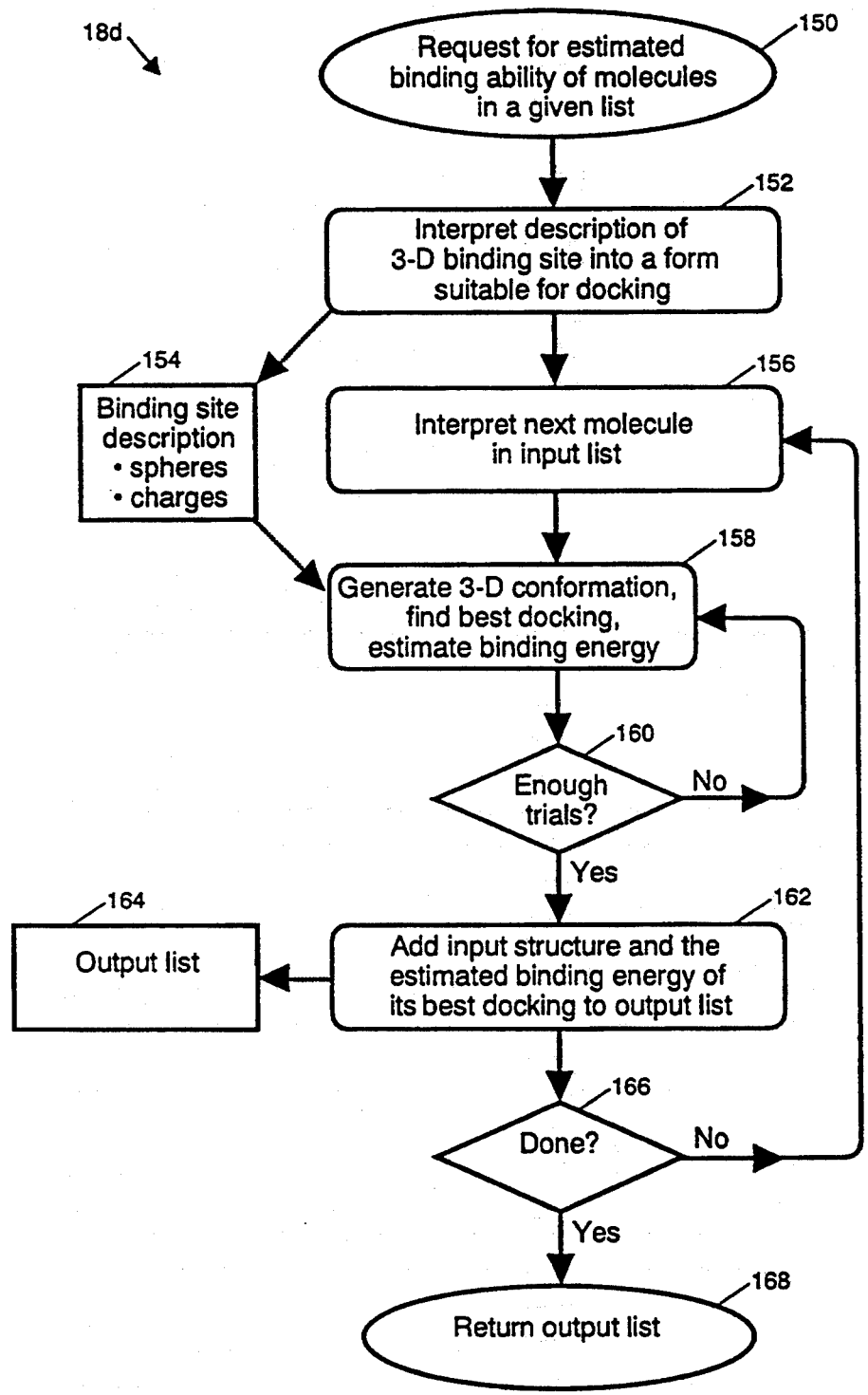
Figure 10:
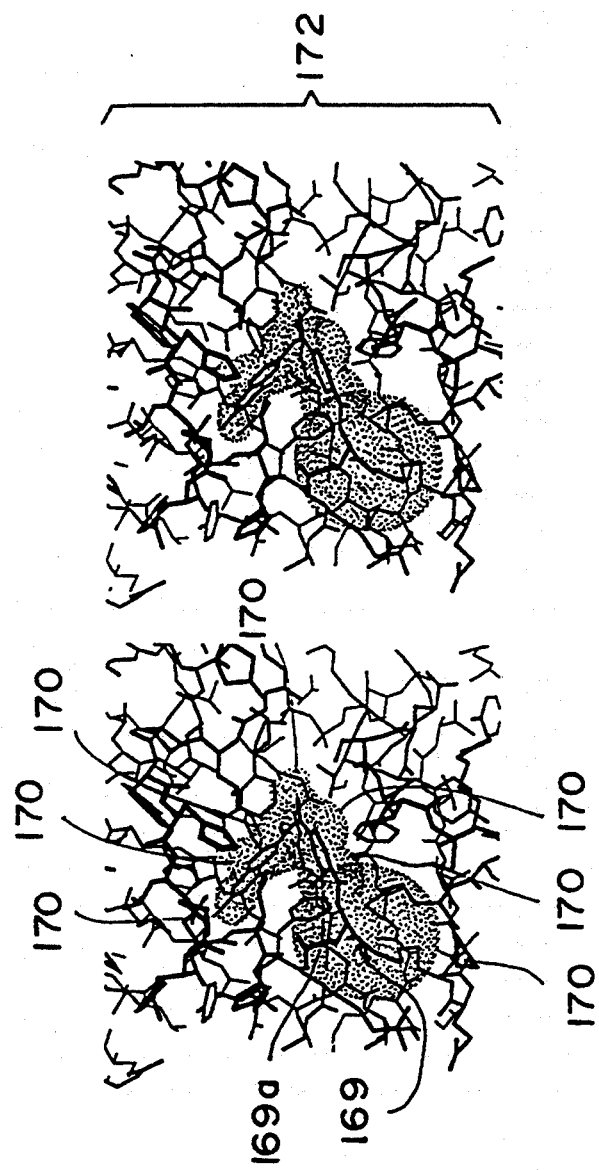
FIG. 10 is a stereoscopic view of a complex binding site, which is shown as dotted surfaces, between the enzyme, dihydrofolate reductase (DHFR), and the chemotherapeutic drug, methotrexate (MTX), which is known in the prior art for its tight binding with DHFR (a stereo viewer facilitates, though is not required, to view this figure as a 3-D image)

Referring now to FIG. 3D, there is shown the step or subprocess 18d for carrying out a fitness function for predicting the theoretical interaction between a drug and an enzyme or protein. The efficacy of the drug to inactivate the enzyme or protein is described in terms of the predicted binding energy between the drug and the enzyme, which may be expressed as kcal/mol. The lower the numerical score of the subprocess 18d for estimating the binding site fitness function, the more effective the evolved drug molecule is predicted to be. In particular, more negative values of kcal/mol indicate greater binding affinity and thus, the greater efficacy of the drug. Initially, it is necessary to develop a model of the enzyme in the form of a 3-D representation of the active or bonding site of the enzyme. FIG. 10 is a 3-D representation of the complex binding site of the well studied enzyme, dihydrofolate reductase (DHFR). Brookhaven Protein Databank, 1992 describes coordinates of DHFR as obtained by X-ray diffraction studies of DHFR crystal structures.

The subprocess 18d starts in step 150, which receives a request that the list of molecules of the present population be evaluated by the estimated binding energy fitness function. Step 150 also enters the 3-D representation of the target binding site of the enzyme. Subprocess 18d evolves the molecular structure of a drug, which will bind tightly with the enzyme's binding site. Next step 152 converts the model or representation of the binding site into a digital data structure, which may be readily compared by step 158 with the molecular structure of each of the drug molecules of the current generation. The complex binding site defines a surface, which encloses a receptor volume into which the object molecules must fit. The above referenced article of Kunst et al. describes a method of defining that receptor volume by a collection of spheres of varying sizes. FIG. 10 shows a series of spheres 170a–g, which are tightly fit within the volume and thus define a receptor volume or binding site 170. Step 152 additionally produces partial charge information in a binding site description 154 for use in the evaluation step 158. Step 152 of constructing the digital description of the binding site description 154 needs to be performed only once during the repetitive execution of the evolving method 10.

Step 156 calls the next object molecule (drug) of the current generation to be compared in step 158 with the digital description of the binding site provided by step 152. Step 156 interprets or converts the communicated representation of each molecule, e.g., a SMILES representation, into data suitable for use by step 158. Step 158 compares the drug and enzyme molecules by conformational analysis to determine the fit of the drug molecule to the binding site description 154 of the enzyme molecule. "Program 159: DGEOM", *Quantum Chemical Program Exchange,* Blaney, J. M., University of Indiana, Bloomington, Ind. (1990) describes a method of generating molecular conformations using distance geometry methods, called DGEOM, which was implemented in this embodiment of the invention. Along with geometric constraints, the distance geometry method allows conformation optimization taking other factors into account, such as internal strains, hydrogen bonding, and other intermolecular electrostatic interactions. Step 158 is repetitively run a given number of times T, e.g., 20, to randomly sample conformations of each molecule. In each of the T trials, step 158 randomly constructs a 3-D representation or model of the molecule. Each atom of the model is assigned a position space represented by three coordinate numbers. Each such model is fitted into the binding site as represented by the spheres 170a–g of FIG. 10. Step 158 computes the fitness score in terms of a theoretical binding energy of Kcal/mol based on how well the model fills the spheres 170, i.e., stearic shape fitting, and the electrostatic interaction between the charges associate with the atoms of the model and those of the receptor molecule. The predicted binding energy is taken as the best numerical score, i.e., the most negative value, realized during the T runs of step 158. Step 160 determines when step 158 has repeated T times, before step 162 adds the input structure and the best value of the binding energy to an output list 164. Then, step 166 determines whether each of the N object molecules in the current population has been subjected to the binding energy fitness function, before returning the output list to the next recording step 24 of the evolving method 10 as shown in FIG. 1.

Figure 11A:
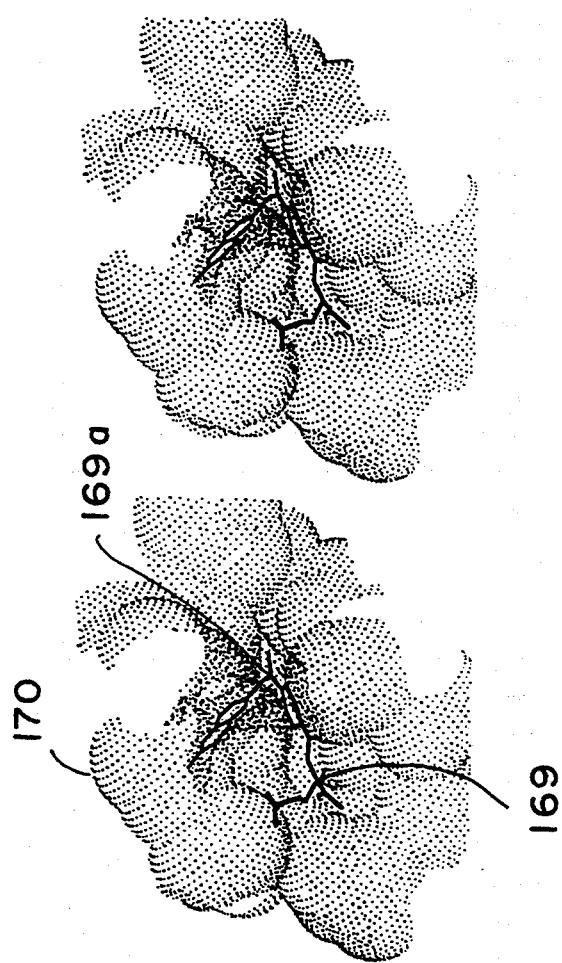
FIGS. 11A and B are respectively a stereoscopic, head-on view of the exterior of and a cutaway view of the binding site of DHFR, which is represented as a dotted surface at twice the van der Waals radius, and the drug MTX, which is disposed in its binding conformation within the binding cavity.
Figure 11B:
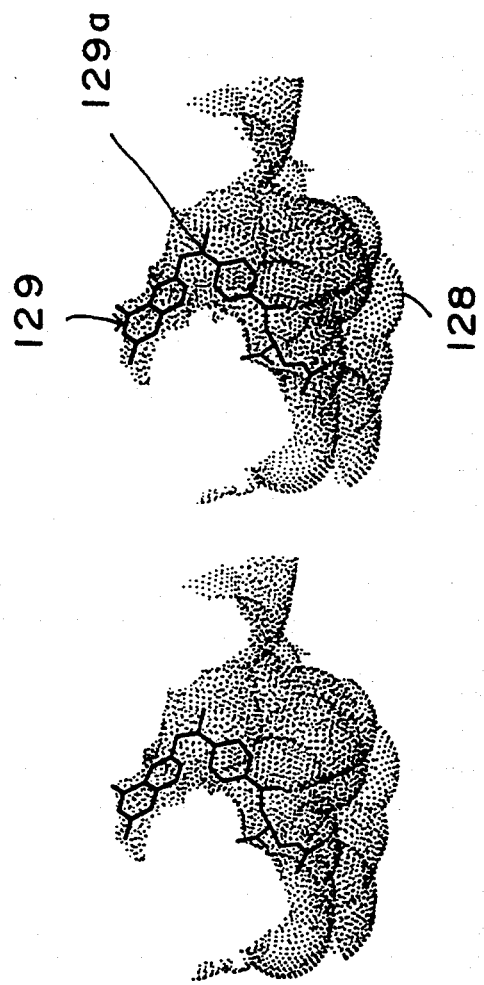

To determine the effectiveness of the evolving method 10 and, in particular, using the subprocess 18d for carrying out estimated binding energy fitness, binding energies were estimated for known, well studied molecules and for an object molecule evolved by the method 10 and subprocess 18d to bind with a known molecule. Methotrexate (MTX) is a well studied chemotherapeutic drug, which is known to bind tightly with the complex binding site of DHFR. As shown in FIG. 10, a MTX molecule 169 fits tightly within the spheres 170, which define the receptor pocket of the DHFR molecule 172. The MTX molecule 169 has as shown in FIG. 10, a pteridine ring system 169a. FIGS. 11A and B show the MTX molecule 169 and the 2X van der Waals surfaces of the spheres 170a–g. The DHFR molecule 172 has been removed from FIGS. 11A and B, and is represented in this figure by the van der Waals surfaces. FIGS. 11A and B show best that the MTX molecule 169 has a sharp bend 169a to fit extremely tightly within the spheres 170a–g, which defines the binding site of the DHFR molecule 172. The subprocess 18d for predicting the binding energy fitness function achieved a bound conformation of the MTX molecule 169 and predicted a binding energy of −47 kcal/mol, which is in the range observed, and is one of highest binding energies observed between molecules.

The evolving method 10 was used with the binding energy fitness function subprocess 18d to evolve a new molecule, which would bind tightly with the DHFR molecule 169. Molecular evolution was initiated using the DHFR molecule 169 as a target with an initial population of 20 molecules containing eight heavy atoms each. The molecular structure 174 shown in FIGS. 12A and B, which evolved using the binding energy fitness function subprocess 18f, is an unsaturated polyamine, which appeared in generation 18 with a predicted binding energy of −131 kcal/mol. The fitness score included: stearic shape fitting and electrostatic interactions. This structure 174 matches both the outer surface and inner binding pocket defined by the spheres 170 exceptionally well.

Figure 3E:
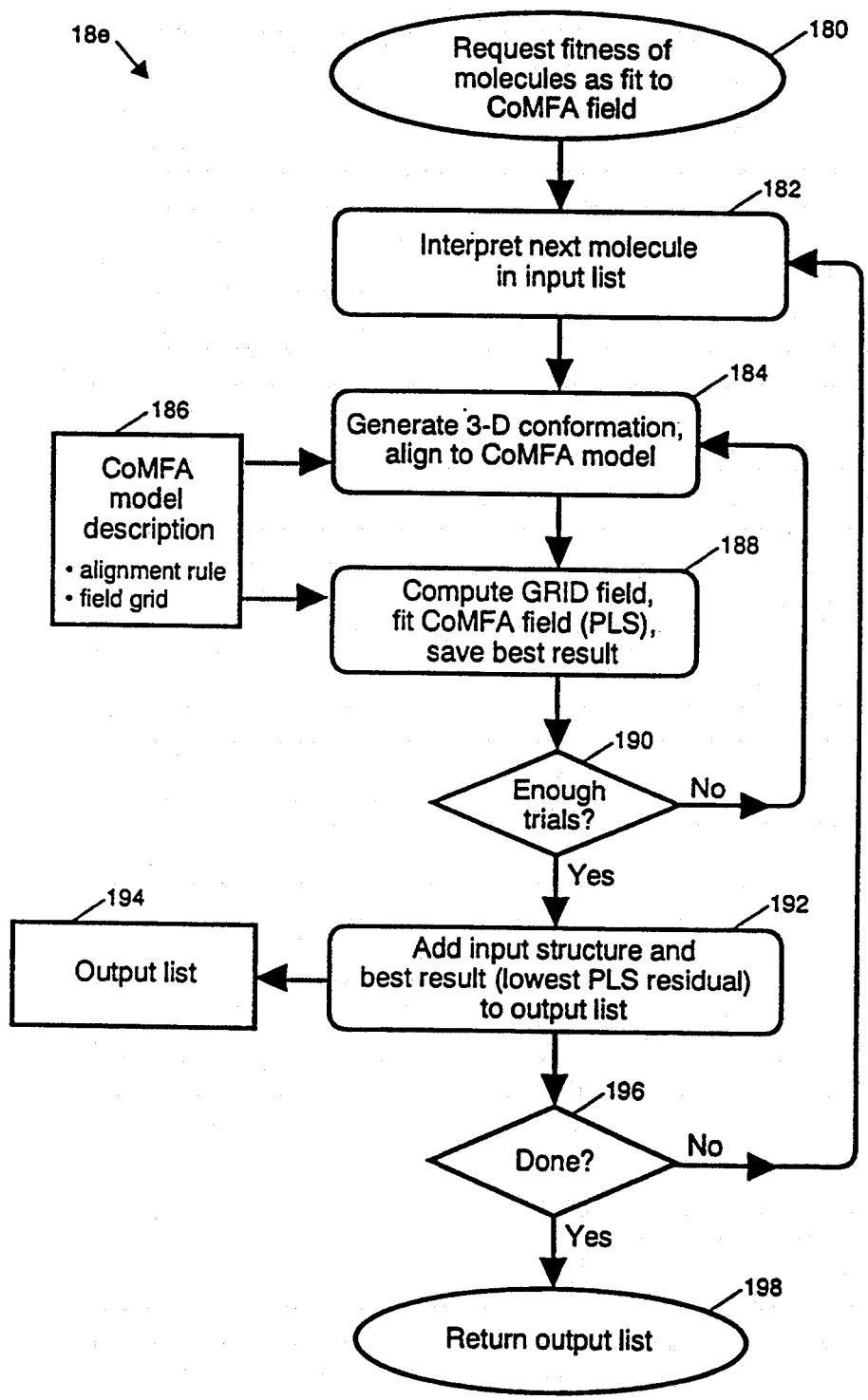

Referring now to FIG. 3E, there is shown the step or subprocess 18e for carrying out a fitness function for computing the fit of molecules using Comparative Molecular Field Analysis (CoMFA). CoMFA is a method for producing a 3-D map of how a known molecule might fit a presumed receptor site, based on constructing conformations of molecules which are known to bind to the site. CoMFA could be used to predict how well a molecule fits into a presumed receptor site which is not dependent upon knowing either the 3-D coordinates of the atoms forming the receptor site or the identity of the receptor molecule. CoMFA builds on two pre-existing technologies: GRID, an algorithm which provides net attractive-repulsive values at equally-spaced points about a molecule, and PLS (partial least squares), an algorithm which allows fitting under-determined sets of linear equations. The details of CoMFA operation are described in U.S. Pat. No. 5,025,388 of Cramer et al., which is incorporated herein by reference. The relevant aspect is that CoMFA provides a model for ligand fitness which consists of a molecular field in space (values at lattice points) and a method for aligning molecules in that field. These components comprise the CoMFA model description which is represented as a data object 186 in FIG. 3E. When a subprocess employing CoMFA is used with the molecular genetic algorithm, the subprocess 18e provides a method for generating novel molecules which fit a CoMFA field.

In operation, the subprocess 18e is very similar in operation to the fitness function implemented by subprocesses 18c and 18d which also produce molecules which optimize fits given 3-D constraints. The subprocess 18e starts in step 180 with a request for the subprocess 18e employing the CoMFA fitness function on a list of molecules of the present population. Next, step 182 converts each molecule in turn from a SMILES representation into a corresponding molecular graph. A loop comprising steps 184 and 188 is executed a fixed number of times as determined by step 190. In each loop, step 184 constructs a different conformation using the distance geometry method described for the subprocesses 18c and 18d shown in FIGS. 3C and 3D. Additionally, step 184 fits or aligns the constructed conformation to the CoMFA model or grid, which is defined by the CoMFA model description 186. Next in each loop, step 188 computes the field about the molecule and evaluates the fit of the molecular field to the CoMFA model field. This procedure may be modified slightly if the CoMFA model specifies the "Field Fit" method for alignment, in which case alignment is done at the same time as the fields are compared. In any case, fitness is taken to be the sum of the squares of the residual errors, which are calculated by the PLS portion of the CoMFA method as explained in the noted Cramer et al. patent. After all trials are completed as determined by step 190, the tested molecular structure with the best fit with the CoMFA model, i.e., the structure with the lowest residual error, is added to the output list 194 by step 192 and the next molecule is processed by step 196. When all of the molecules have been evaluated, the output list 194 is returned to the recording step 24 of the evolving method 10 as shown in FIG. 1.

As described above, the CoMFA fitness function subprocess 18e is generally much less efficient than the previously-described subprocess 18c using the pharmacophore fitness function and subprocess 18d using the binding fitness function when a simple alignment rule is not available. A distance-geometry-based method for generating 3-D conformations which simultaneously aligns and fits the CoMFA field while producing chemically reasonable conformations would reduce or eliminate the need to sample a large number of conformations as by steps 184, 188 and 190. To date, attempts to do this have proved unsuccessful. Even so, molecular evolution combined with CoMFA analysis offer interesting opportunities for de novo design when other methods are not applicable.

Figure 3F:
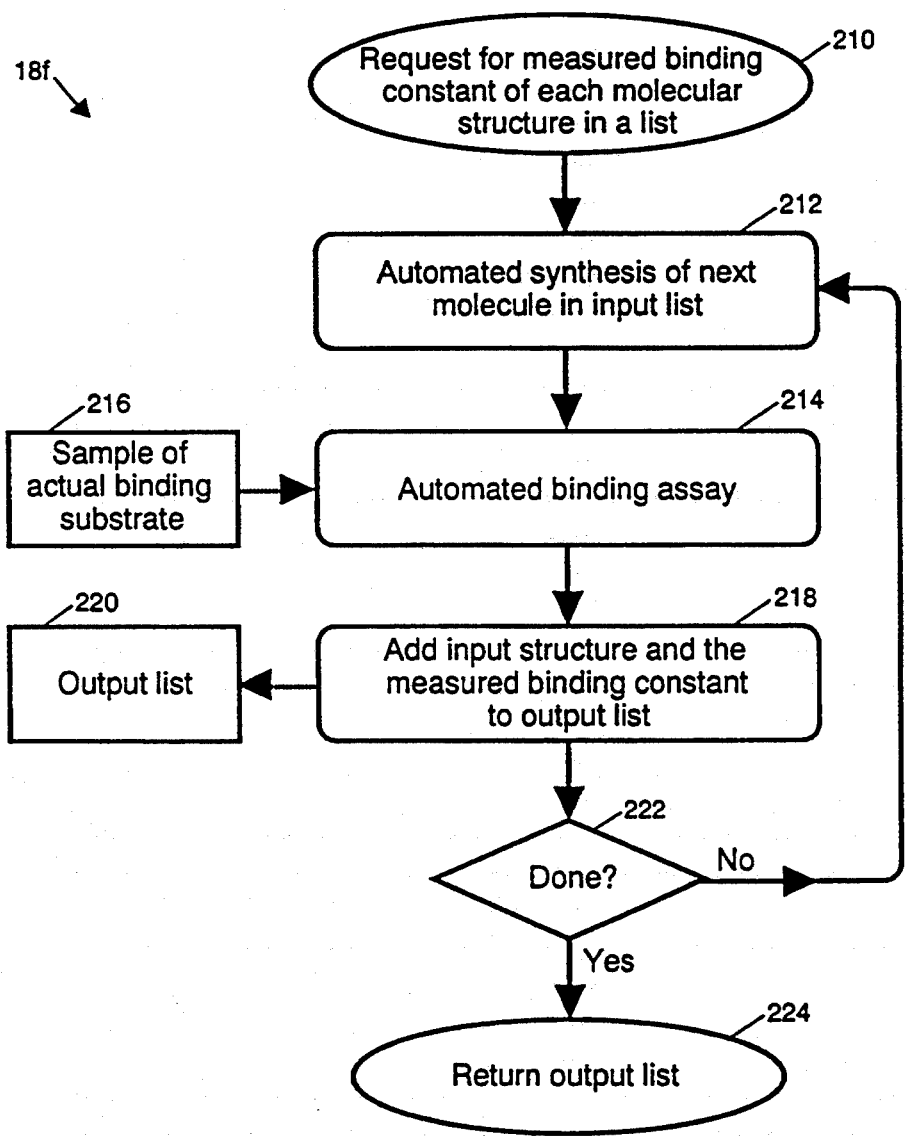

Referring now to FIG. 3F, there is shown a subprocess 18f for carrying out a binding energy fitness function, not by estimating the binding energy as subprocess 18d does, but rather by actually synthesizing each molecule of a generation and then measuring its binding energy with the enzyme or protein to be attacked. Initially, step 210 receives the request that the binding energy of each molecule in a population be made, before step 212 synthesizes each molecule in the given list. Step 214 introduces each synthesized molecule one-at-a-time to an actual sample of the enzyme 216 and assays the actual binding energy of the molecule to the enzyme. Step 218 outputs the input structure and its measured binding constant to an output list 220. Step 222 determines whether each molecule in the given list has been synthesized and assayed; if so, step 224 returns the output list 220 to the next recording step 24 of the evolving method 10 as shown in FIG. 1. This subprocess 18f has the advantages that its results are based on actual measurements, are not subject to approximations and errors made by fitness functions implemented in software and will produce a population of real molecules, which, if successful, are proven to bind with the target molecule.

Figure 3G:
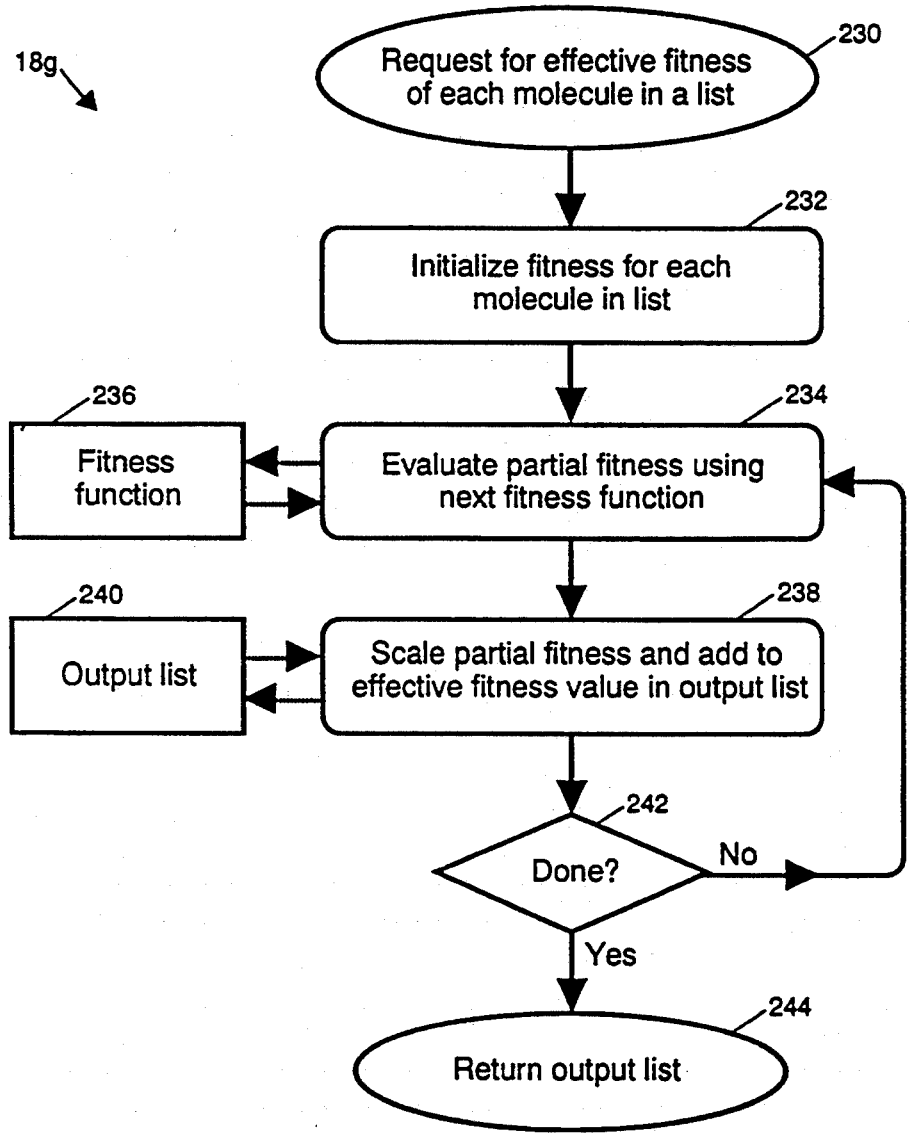

Referring now to FIG. 3G, there is shown the step or subprocess 18g for carrying out a composite fitness, which may selectively comprise one or more fitness functions. Illustratively, the selected fitness functions may take the form of the fitness functions described as subprocesses 18a-18f as shown in FIGS. 3A-3F. Using subprocess 18g, the evolving method 10 as shown in FIG. 1 can not only optimize molecules to fit an arbitrary fitness function in the form described above, but can also optimize a fitness function which is a linear combination of other fitness functions, called a "composite fitness function". As shown in previous examples, any fitness function can be composed of a multitude of components, e.g., the pharmacophore fitness function 18c is comprised of the sum of bounds violations as carried out by step 138 of FIG. 3C. Composite fitness functions differ from such fitness functions only in that the component fitness functions are guaranteed to operate independently of each other. This allows a wide variety of ad hoc functions to be combined to provide the pressure to drive the evolving molecular populations to the desired set of properties. Such ad hoc fitness functions can be used together to design drugs, which have a plurality of corresponding properties tailored to make the drug effective. For example, the subprocess 18g could sequentially apply to each molecular structure of a population selected fitness functions. In addition to the binding energy fitness function described with respect to FIG. 3D, the composite fitness function would further comprise ad hoc functions to evolve the molecular structures towards corresponding sets of properties. In the context of drug design, the ad hoc functions could reduce entropy to render the molecule more effective and faster acting, reduce photooxidation and thus improve the shelf life of the drug, reduce hydrolysis and thus its reaction with water, improve its resistance to digestion and thus make it suitable for oral delivery and optimize its hydrophobicity so that the resultant molecule would be resistant to fatty tissue and be readily transported into desired cell types.

The subprocess 18g starts in step 230 by receiving a request for effective fitness of a list of molecules with respect to a number of fitness functions. Step 132 initializes the fitness of each molecule in the list to a value indicating "not set". Such initialization is needed to handle the possibility that some of the component fitness functions are unable to process one or more of the molecules in the population. Step 234 generates a request to the fitness function 236, e.g., step 150 in FIG. 3D. The subprocess 18 implementing the first requested fitness function is executed to provide a first partial score. Step 238 scales the partial fitness score by the amount specific to that fitness function and adds it to the composite fitness score for the appropriate molecules in output list 240. Scaling is required to adjust the relative magnitudes of the results of different fitness functions to common units so that they may be added together meaningfully. Step 242 determines if all fitness functions have been evaluated; if not, steps 234 and 238 are repeated using different fitness functions 236. When all of the required fitness functions have been evaluated, an output list 240 is returned to the recording step 24 of the evolving method 10 as shown in FIG. 1.

Figure 12A:
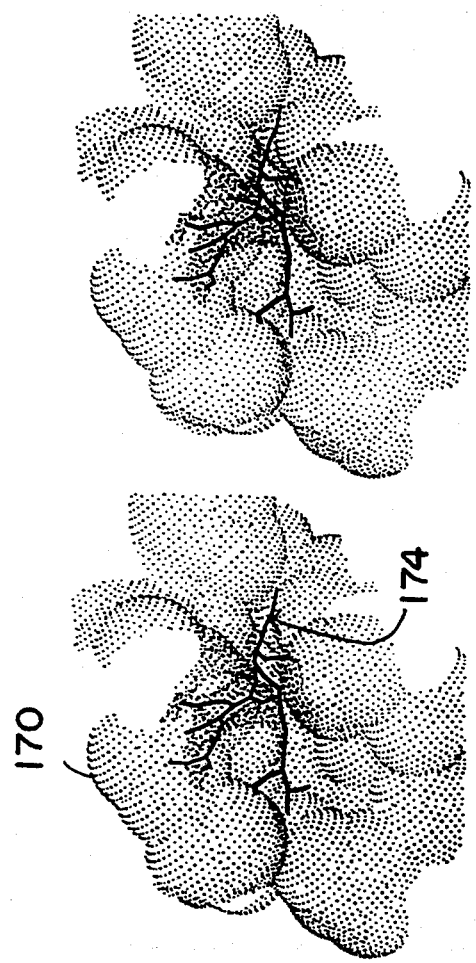
FIGS. 12A and B are respectively a stereoscopic, head-on view of the exterior of and a cutaway view of the binding site of DHFR, and a polyamine, which evolved after 18 generations of the evolving method of FIG. 1 using the binding energy fitness function of FIG. 3D.
Figure 12B:
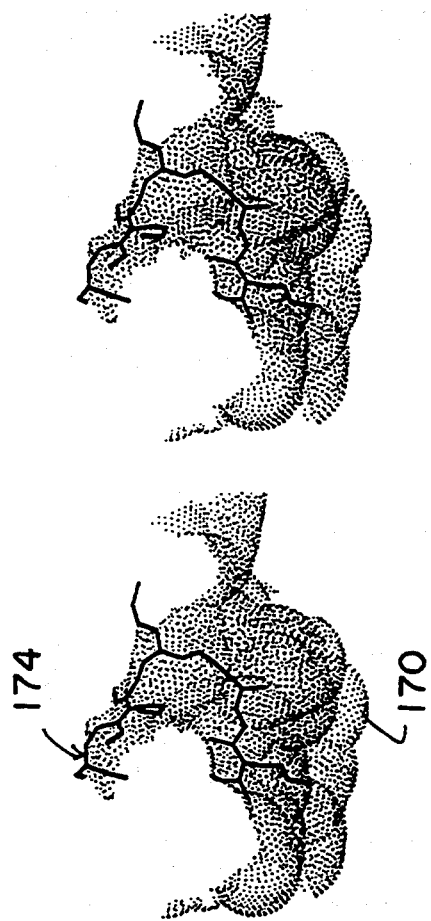

To demonstrate the effectiveness of the composite fitness function subprocess 18g, the molecular structure 174 shown in FIGS. 12A and 12B was further evolved using an additional fitness function to form a composite fitness function. The additional fitness function seeks to minimize the number of non-ring bonds in a molecule by assigning a penalty of 1.0 kcal/mol for each non-ring bond. This function was combined with fitness function 18d of FIG. 3D using the composite fitness function 18g of FIG. 3G. The effect of the additional fitness function is to strongly bias the molecular evolution towards populations of molecules containing rings. (Molecules containing many rings have a lower conformational entropy than similar non-cyclic molecules, i.e., given that both can conform to a binding site equally, a highly cyclized molecule will have many fewer non-binding conformations than an equivalent non-cyclic molecule, and will typically bind faster.) This modification reduces the acceptable universe of molecules and makes the design problem harder, i.e., to construct molecules containing mostly rings which fit the DHFR binding site geometrically and electrostatically. The problem is especially difficult because the geometry of ring systems is very constrained compared to chains.

Figure 13B:
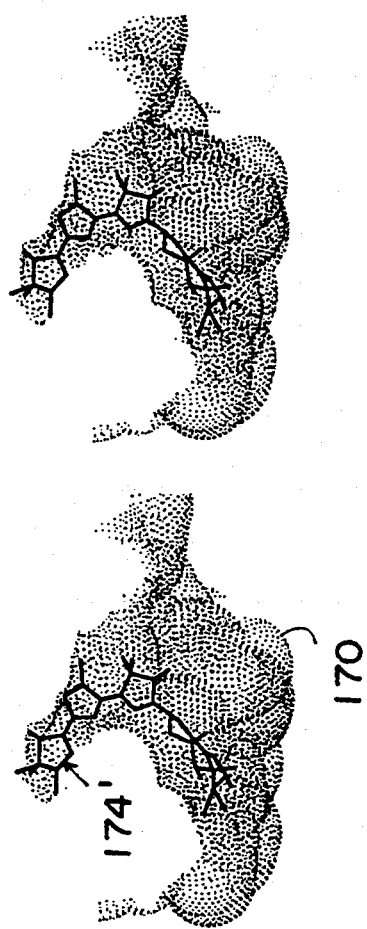
FIGS. 13A and B are respectively a stereoscopic, head on view of the exterior of and a cutaway view of the binding site of DHFR, and a polycyclic polyamine, which evolved after 130 generations of the evolving method of FIG. 1 using the composite fitness function of FIG. 3G.

FIGS. 13A and 13B show an evolved molecular structure 174' which first appeared in generation 130, after 11 hours running time on a SGI Crimson R4000. The evolved molecule 174' is almost completely cyclic and contains 6 alicyclic rings, 27 ring bonds, and 18 non-ring bonds; even so, the molecule 174' fits the binding site extremely well. The fitness score for the molecular 174' was −46.73, but this is not strictly comparable to binding energy predictions because it is a result of a composite fitness function.

The evolved molecular structures shown in FIGS. 12 and 13 demonstrate the ability of the molecular evolution method 10 of this invention to produce molecules which optimize extremely difficult and complex functions. The success of the subprocess 18g employing a composite fitness function illustrates that additional, ad hoc functions can be accommodated as well, which might be used for producing molecules which have additional desired properties such as solubility, hydrophobicity, and synthetic feasibility.

Figure 4:
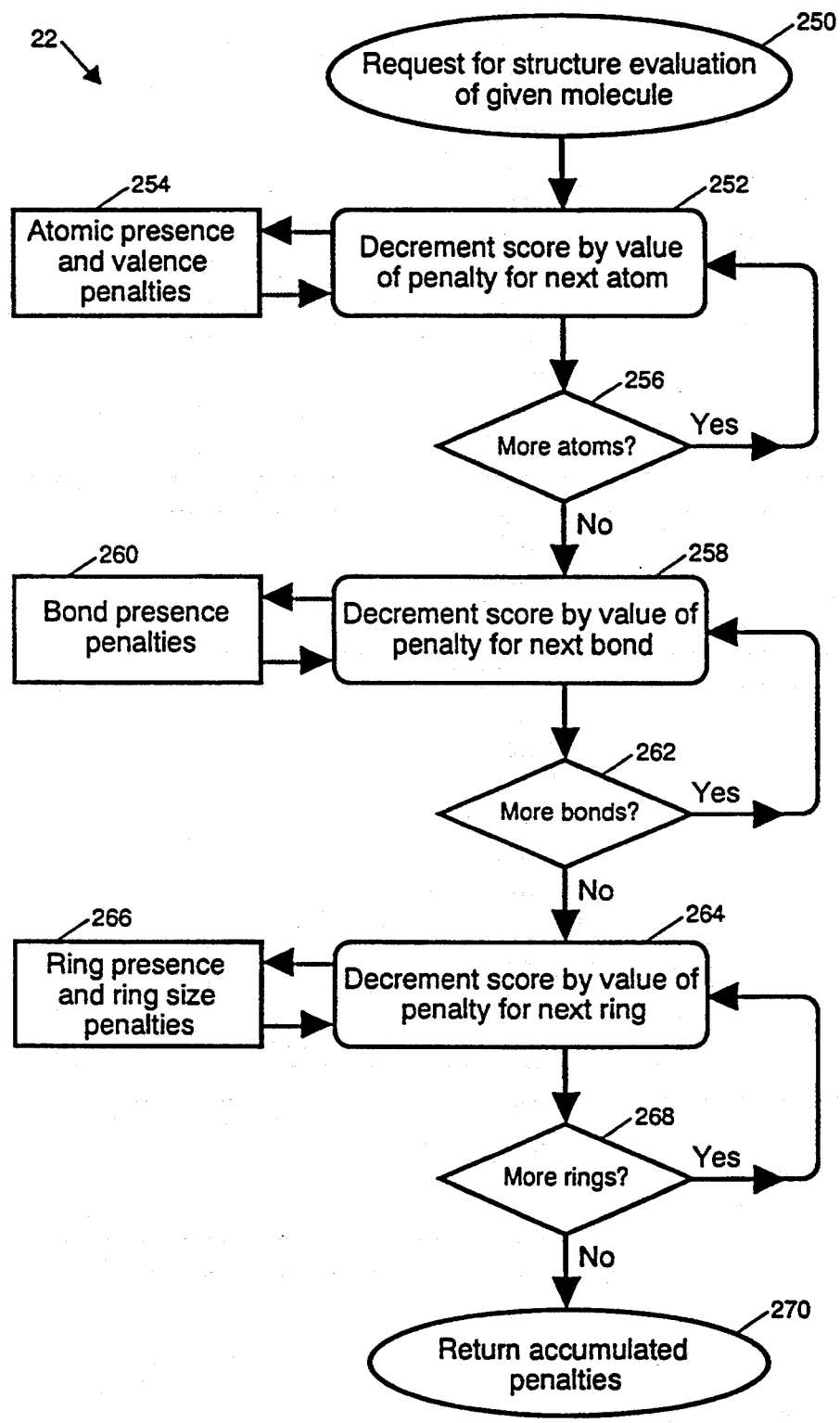
FIG. 4 is a more detailed, low level flow diagram of a method of evaluating the viability of a given molecular structure as generally indicated by step 22 of the high level flow diagram of FIG. 1.

Referring now to FIG. 4, there is shown a more detailed, lower level flow diagram of the step or subprocess 22 shown generally in FIG. 1, for determining the viability of an object molecule. When working with randomly-generated representations of molecules as produced in step 12 of FIG. 1, there is a need to evaluate the "chemical reasonableness" or viability of the molecules that are evolved. This is true even if all molecules in the population are "valid" in the sense that all the electrons add up and they represent a theoretically possible molecule. The reason is that most combinations of atoms and bonds do not represent a molecule which is stable in the real world, i.e., if it did exist, it would spontaneously decompose to something else. Furthermore, many molecules in isolation do not have practical applications, e.g., for pharmaceutical applications, molecules which react violently with water are not suitable drug candidates. In the molecular evolution method 10, chemical reasonableness evaluation can theoretically be done by solely by the fitness function, i.e., unreasonable molecules are assigned a very poor fitness score. In practice, it is convenient to limit the fitness function structural evaluation to assessments of molecular suitability, and to provide a separate chemical reasonableness evaluation in the evolution method 10. This approach eliminates the need for adding such an evaluation to each fitness function that will be used.

Initially, step 250 receives a request to evaluate the structure of one molecule of the current population at a time. Table 254 comprises a list of reasonable atomic environments based on normal valence assumptions, i.e., commonly observed atomic environments. Step 252 evaluates each atom one at a time and assigns penalties for atoms which occur in environments which are not commonly observed in nature. Beginning in step 252, a composite score is kept of the penalty points. Step 256 determines when the last atom has been evaluated to continue the subprocess 22 in step 258. In similar fashion, steps 258 and 264 evaluate the object molecule and add penalty points for unreasonable configurations respectively of bonds and the presence and size of rings. The penalty points for unreasonable bonds and rings are respectively added to the running score in steps 258 and 264. After each ring has been evaluated as determined by step 268 and the score of penalty points has been totalled in step 264, the accumulated penalty score is returned by step 270 to the next record step 24 of the evolving method of FIG. 1.

Figure 5:
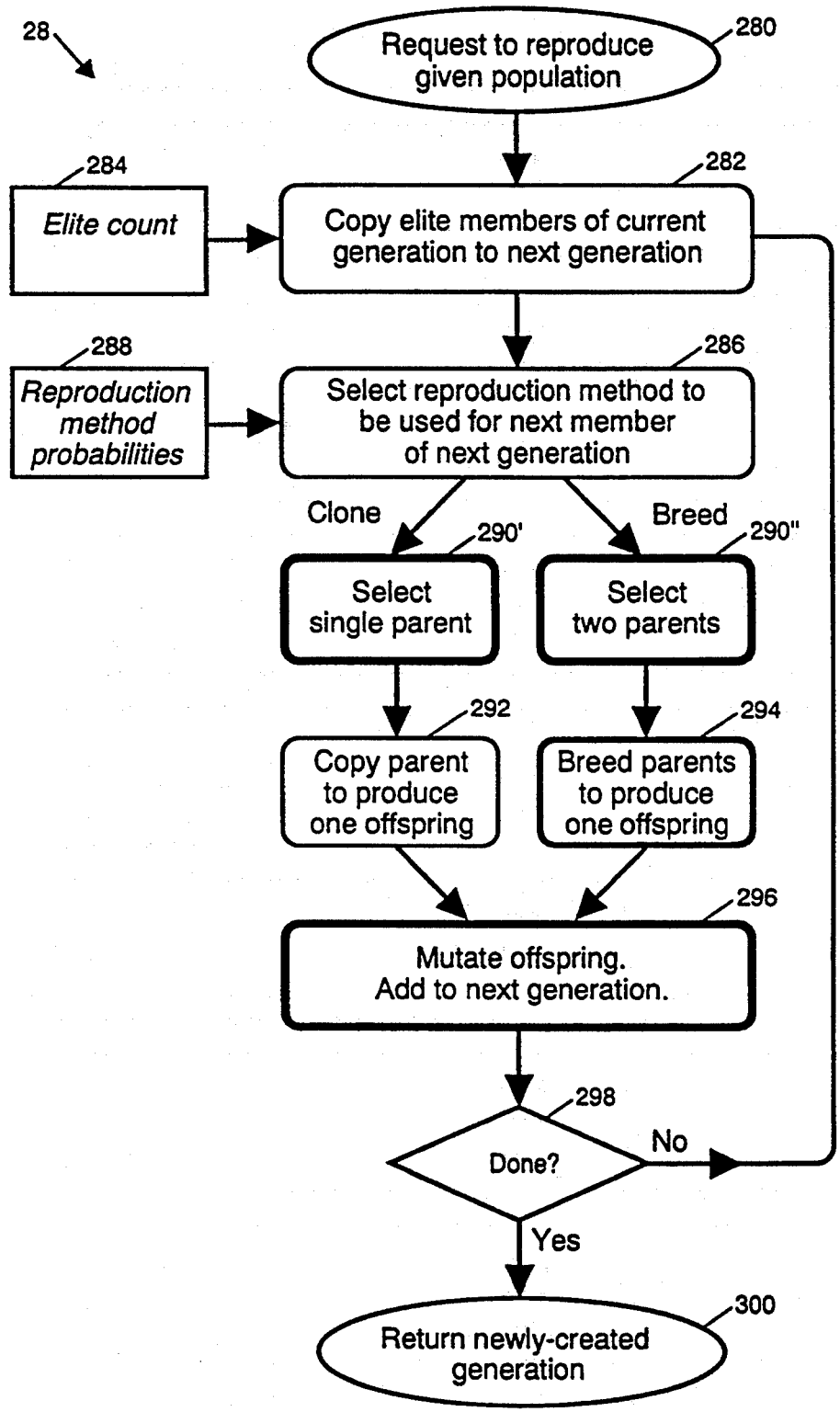
FIG. 5 is a more detailed, intermediate level flow diagram of a method of evolving a given generation of molecules to reproduce the next generation of molecules as generally indicated by step 28 of the high level flow diagram of FIG. 1.

In FIG. 5, an expanded flow chart of the step 28 of reproducing of FIG. 1 is shown. The reproduction step 28 is a method for producing the next generation from a population in a manner biased by the fitness scores of its individual members. To successfully evolve a generation of molecules, a number of potentially-conflicting goals must be achieved. Desirable attributes must be passed on to the next generation, synergistic attributes of different molecules in the population must be allowed to combine, new features must be introduced, diversity within the population must be maintained at a reasonable level, and undesirable features must be selected against. To produce a practical solution, it is important to accelerate evolution well beyond the rates that are found in nature (typically populations of millions of members of the animal kingdom evolving over many thousands of generations).

Initially, step 280 receives a request that the current generation of molecules be reproduced or evolved. Then, step 282 selects and copies without change elite molecules from the last generation to the next. The elite molecules are determined by the numerical score awarded to each molecule by the fitness function subprocess 18. A number E of the object molecules of the last generation with the highest numerical scores are identified. Step 284 determines the number E of molecules to be copies. The object of elitism is to insure that the best existing features are not lost in the evolving generation. In the implementation described here, the number E of such elite members can be set from zero to the entire population. In the examples of the evolved molecules shown in FIGS. 9, 11A and B, 12A and B and 13A and B, the "elite count" or number was set to one, i.e., only the best member of each generation was copied intact to the next generation.

Next, step 286 selects which of the cloning or breeding methods is to be used, in accordance with the frequencies in the table 288, which are adjustable parameters. If cloning is selected, the reproducing method 28 proceeds to step 290', which selects a single "parent" molecule before step 292 copies or clones that parent to produce a single "child" molecule. If breeding is selected in step 286, step 290" selects "parent" molecules in a manner to ensure that the "parent" molecules are not identical. The two selected "parent" molecules then breed in step 294 to produce one "child" molecule. As will be explained below with respect to FIG. 7, breeding selects attributes from each of the selected "parent" molecules and combines them to form the "child" molecule. Before adding the "child" molecule to the next generation, step 296 mutates the molecular structure of the "child" molecule. As will be explained below with respect to FIG. 8, selected atoms and/or bonds may be added, deleted or changed by mutation. After a molecule has been mutated, step 298 determines whether all of the molecules for the next population have been reproduced. If not, the subprocess 28 returns to step 282 to evolve the next molecule. If all of the molecules have been evolved, step 300 passes the evolved molecules to the next generation.

Figure 6:
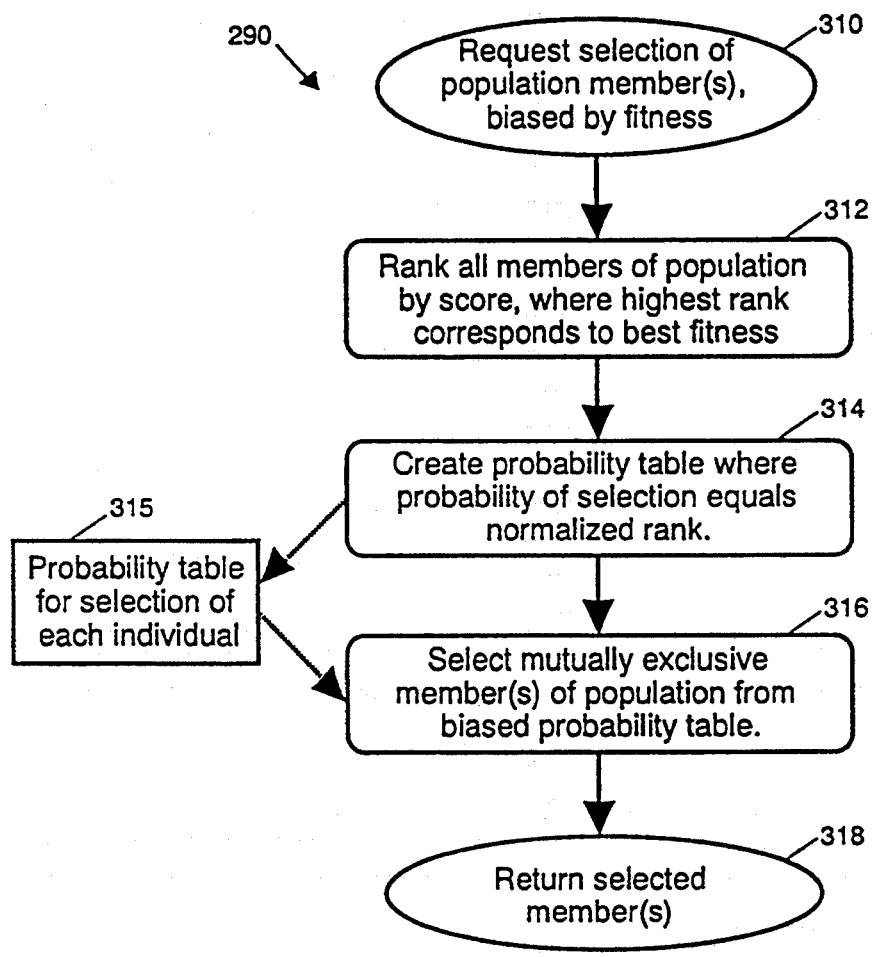
FIG. 6 is a still more detailed, low level flow diagram of a method of selecting the "parent" molecules to be reproduced as generally indicated by step 290 of the intermediate level flow diagram of FIG. 5.

Referring now to FIG. 6, steps 290' and 290" are shown as an expanded flow chart, appreciating that step 290" selects two "parent" molecules for breeding and step 290' selects only one "parent" molecule for cloning. First, step 310 receives a request for a biased selection of one or more parents, a list of the molecules of the current population, and the related fitness scores which are calculated by the fitness function 18. Next, step 312 ranks the object molecules by the numerical fitness function scores, where the highest ranked molecules have the best fitness scores. Then, step 314 creates a probability table 315 where the probability of selection equals the normalized rank of the molecules. The rank order method used here for biasing selection probability means that the numeric value magnitudes of the fitness scores is not important, only their rank. Rank order is used rather than fitness scores because there is generally not a linear relationship between fitness scores and the desired molecular "quality". Also, using rank order maintains a relatively constant selection pressure as the population converges. Then, step 316 selects the two "parent" molecules or one "parent" molecule depending on the whether the "child" molecule is to be bred or cloned, from the probability table 315. If two "parent" molecules are selected, they are mutually exclusive. The selected "parent" molecule or molecules is then passed by step 318 to either step 292 or step 294.

Figure 7:
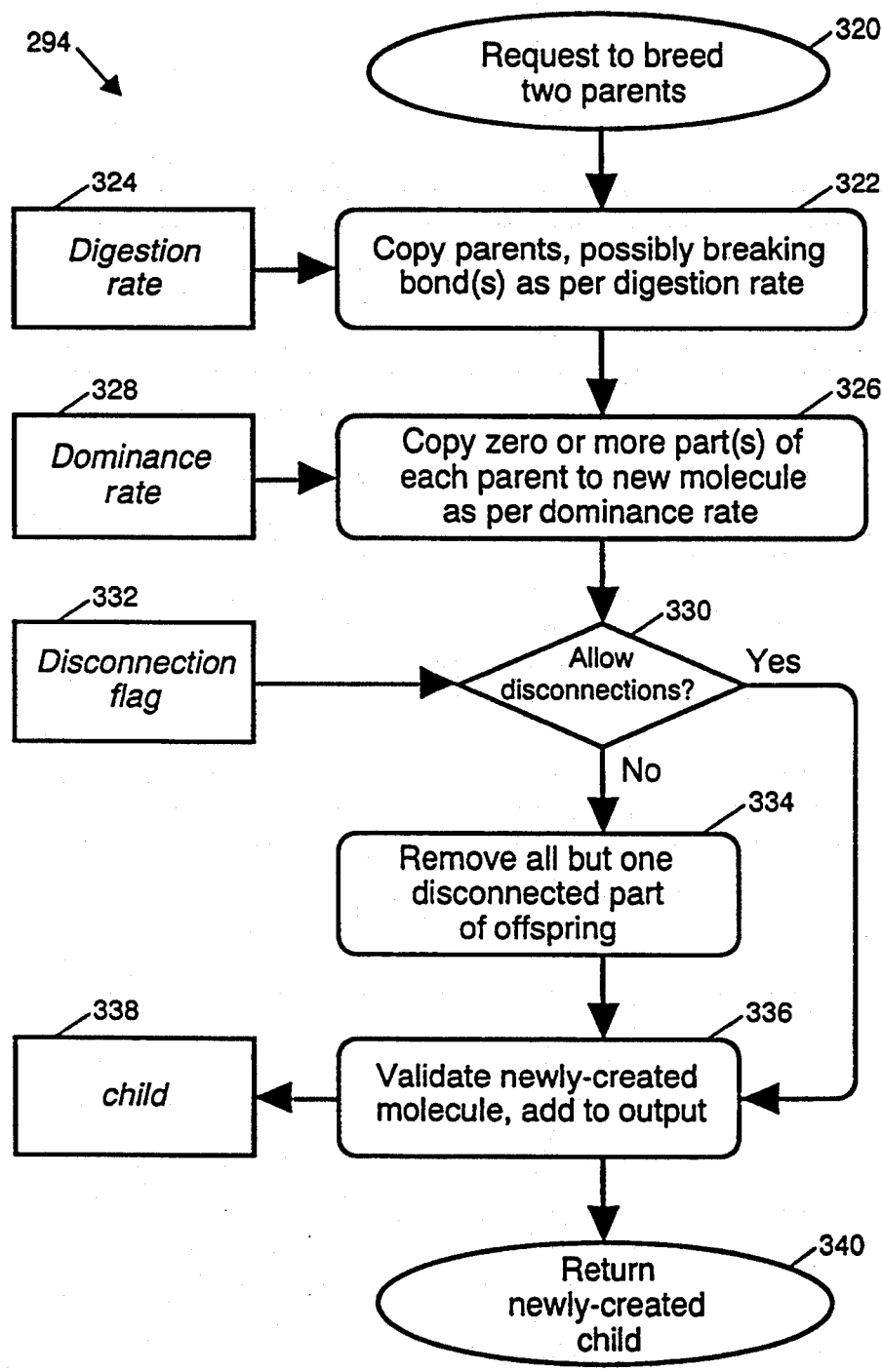
FIG. 7 is a still more detailed, low level flow diagram of a method of "breeding" two "parent" molecules to reproduce a single "child" molecule as generally indicated by step 294 of the intermediate level flow diagram of FIG. 5.

Referring to FIG. 7, step 294 of breeding is expanded as a more detailed, lower level flow diagram. The steps of breeding of FIG. 7 are not suitable for use with external representations, but rather must operate on the digitally encoded molecular graph. Initially, step 320 receives the request to breed two "parent" molecules. Next, step 322 breaks the bond(s) between the atoms of the "parent" molecules in accordance with the "digestion" rate set in step 324. The "digestion" rate controls the fraction of the bonds to be broken in each "parent" molecule and is an adjustable parameter. Next, step 326 copies a fraction or part of the broken molecular fragments to be incorporated into the structure of the breed "child" molecule. This fraction is set in step 328 as the "dominance" rate. Step 332 sets a flag which controls whether the molecular fragments may be reformed. If disconnected structures are not allowed, step 334 selects a single connected molecule fragment to be the "child" molecule. Then, step 336 adds the bred "child" molecule to an output list 338, before step 340 returns the output list 338 to the next step mutating step 296 of FIG. 5.

Figure 8:
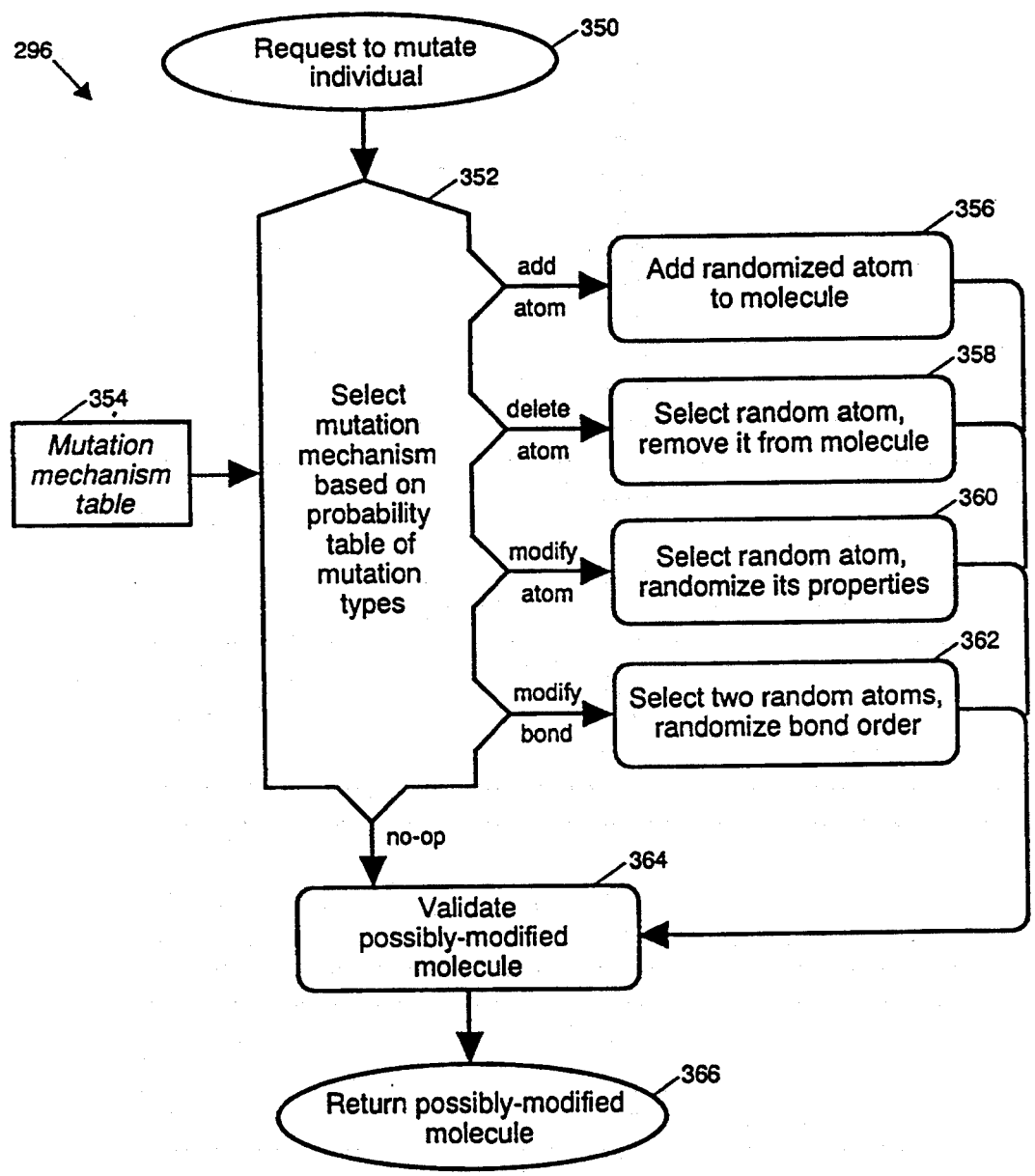
FIG. 8 is a still more detailed, low level flow diagram of a method of mutating a "child" molecule by selectively adding, deleting or modifying an atom, or modifying the bond between two randomly selected atoms as generally indicated by step 296 of the intermediate level flow diagram of FIG. 5.

Referring to FIG. 8, the subprocess 296 for mutating the structure of the evolved "child" molecule is shown in greater detail as a lower level flow diagram. Mutation of the bred or cloned "child" molecule is the primary source of diversity in the object molecules of the next generation. In this illustrative step 28 of reproducing, molecules are represented as molecular graphs, whereby mutation operates directly on the molecular graph. The mutation step 296 operates on a single bred or cloned "child" molecule to produce a single, possible mutated "child" molecule. Initially, step 350 receives a request to mutate a single bred or cloned "child" molecule by any number of mutation mechanisms, e.g., inactive mutation carried out by directly moving to step 364, atom mutation by step 356, atom deletion by step 358, atom transmutation by step 360 or bond modification by step 362. Only one mutation mechanism is used on one molecule per mutation. Probability rates for each of these mutation mechanisms are set in the table 354 dependent on how the mutation process is desired to be run and/or the type of object molecule to be evolved. Upon receipt of a request from step 350, step 352 accesses the mutation mechanism table 354 to determine the set probability rates and based on these rates, randomly selects one of the steps 356, 358, 360, or 362. Step 352 may elect to avoid any of the steps 356, 358, 360 or 362, and thereby avoid mutating the bred or cloned "child" molecule, whereby the bred or cloned "child" molecule is passed intact to the next generation without mutation. The atom insertion step 356 randomly selects a new atom and bonds to be added to the bred or cloned "child" molecule according to the natural frequency of occurrence of atoms and bonds in a primitive frequency table as described above with respect to step 66. The randomly selected atom is added to a randomly selected atom existing in the current molecular graph by a randomly selected bond. The atom deletion step 358 randomly selects an atom in the current molecular graph and removes it. The atom transmutation step 360 randomly selects an atom in the current molecular graph and randomly changes the properties of that atom, e.g., changes the selected atom from C to N. The bond modification step 362 randomly selects two atoms in the current molecular graph and sets it to a random bond order. In other words, an existing bond between two selected atoms of the current molecular graph bond could be created, deleted or modified. For example, bond modification might result in changing a double bond to a single bond. The molecules shown in FIGS. 12A and B, and 13A and B were evolved by selecting the probability rates in the mutation mechanism table 354, the atom insertion step 356, the atom deletion step 355, the atom transmutation step 360 and the bond modification step 362 to respective probability rates of 0% (no mutation), 20%, 20%, 10% and 50%. Because of the random selection and mutation of each object molecule, the mutated molecule is tested in step 364 to determine whether it is viable in a manner similar to that of step 22 described in detail above with respect to FIG. 4. Finally, step 366 returns the resultant, mutated "child" molecule for inclusion in the next generation.

The reproduction method 28 of FIG. 1, as detailed in FIGS. 5-8, contains a number of adjustable parameters, specifically: elite count 284; reproduction method probabilities, i.e., determining in step 288 the rate of cloning vs. breeding; digestion rate, i.e., determining by step 324 the fraction of bonds to be broken during digestion; determining by step 328 the dominance rate; determining by step 332 the disconnection flag; and determining by step 354 the mutation mechanism probabilities. These are provided as adjustable parameters to provide compatibility with a wide variety of fitness functions and to allow control over the rate of the entire process.

In particular, the setting by step 332 of the disconnection flag is typically dictated by the nature of the fitness function(s) used. Disconnected structures are forbidden if a fitness function is meaningless when applied to, or can not operate on, disconnected (multiple) molecules, e.g., a fitness function predicting solubility of a single solute.

Under most circumstances, an important goal of the molecule genetic algorithm is to provide results as efficiently as possible, i.e., to produce acceptable results as quickly as possible. To this end, evolution is accelerated by using: a non-zero elite count, e.g., 1; moderate levels of breeding vs. cloning, e.g., 50:50%; a high digestion rate, e.g., 20%; a low dominance rate, e.g., 0%; and high mutation rates, e.g., 0% inactive mutation. The effect of such settings is to allow large structural jumps in each generation, while elitism promotes generation-to-generation stability. The resultant evolution is highly accelerated, but at a cost of losing some fine tuning of the population. In circumstances where the fitness function is very fast, e.g., a large amount of computing power is available, the best compromise will favor less evolutionary acceleration, e.g., using larger populations with lower levels of cloning, e.g., 10%; lower digestion rates, e.g., 5%; higher dominance rates, e.g., 30%; much lower mutation rates, e.g., 90% inactive mutation; and no elitism, e.g., elite count 0. By using such parameters, molecular evolution will more nearly resemble natural evolution, i.e., slow and comprehensive, but will consume much more resources in terms of compute time.

In considering this invention, it should be remembered that the present disclosure is illustrative and the scope of the invention should be determined by the appended claims.

I claim:

1. A method of evolving a representation of a molecule with a set of desired properties by successively generating a sequence of populations, each of said populations comprising a plurality of member representations of the chemical composition and connectivity of member molecules, said method comprising the steps of:

a) comparing each member representation of a present population of said sequence of populations with said set of desired properties to assign to each compared member representation a numerical value dependent on how closely said compared member representation corresponds with said set of desired properties;

b) selecting said member representations of said present population dependent on their respective numerical values and changing the chemical composition and connectivity of at least one of said selected member representations to be reproduced within a next population of member representations of said sequence of populations, said selecting and changing being performed on a computer; and c) repetitively executing steps a) and b) at least one time, each execution of steps a) and b) producing said next population of said member representations within said sequence of populations.

2. The method to evolve said molecule as claimed in claim 1, wherein there is further included the step of randomly generating a first population of member representations.

3. The method to evolve said molecule as claimed in claim 2, wherein said first population of member representations is compared in accordance with step a) to produce a corresponding set of numerical values and said first population of member representations is selected and changed in accordance with step b).

4. The method to evolve said molecule as claimed in claim 1, wherein said step a) of comparing further comprises a substep of evaluating each reproduced member representation to determine whether it is chemically stable and including in said next population only those member representations which are chemically stable.

5. The method to evolve said molecule as claimed in claim 4, wherein said substep of evaluating is carried out on each member representation of said present population to produce a second numerical value indicative of its chemical stability, said numerical value and second numerical value being combined to produce a composite value, said step b) of selecting said member representations of said present population being dependent upon said composite value.

6. The method to evolve said molecule as claimed in claim 1, wherein said step b) of selecting includes selecting a number of elite member representations of said present population dependent upon their respective numerical values to be reproduced directly into said next population.

7. The method to evolve said molecule as claimed in claim 1, wherein said step b) of selecting includes a substep of selecting a number of parent member representations from said present population of member representations dependent upon their numerical values.

8. The method to evolve said molecule as claimed in claim 7, wherein said step b) of changing includes a substep of producing a selected number of child member representations from said selected number of parent member representations.

9. The method to evolve said molecule as claimed in claim 8, wherein said step b) of changing includes a substep of mutating said selected number of child member representations to provide one of said member representations to be reproduced within said next population.

10. The method to evolve said molecule as claimed in claim 9, wherein said substep of selecting selects one parent member representation, and said step b) of selecting and changing includes a substep of cloning said selected one parent member representation to reproduce a single child member representation within said next population.

11. The method to evolve said molecule as claimed in claim 9, wherein said step b) of selecting and changing further includes substeps of selecting at least two parent member representations and of breeding said two selected parent member representations to produce therefrom a single bred child member representation to be included within said next population.

12. The method to evolve said molecule as claimed in claim 11, wherein said substep of selecting includes a subsubstep of comparing said two selected parent member representations to ensure that said two selected parent member representations correspond to different member representations of said present population.

13. The method to evolve said molecule as claimed in claim 11, wherein said substep of breeding takes selected fragments of each of said two selected parent member representations, and combines said selected fragments to form said single bred child member representation to be reproduced within said next population.

14. The method to evolve said molecule as claimed in claim 11, wherein said substep of mutating includes a subsubstep of providing an atom with randomly determined properties and adding said atom to said single bred child member representation to provide one of said member representations to be reproduced within said next population.

15. The method to evolve said molecule as claimed in claim 11, wherein said substep of mutating includes a subsubstep of randomly selecting an atom of said single bred child member representation and removing it to provide one of said member representations to be reproduced within said next population.

16. The method to evolve said molecule as claimed in claim 11, where said substep of mutating includes a subsubstep of selecting an atom of said single bred child member representation and replacing it with an atom of randomly determined properties to provide one of said member representations to be reproduced within said next population.

17. The method to evolve said molecule as claimed in claim 11, wherein said substep of mutating includes a subsubstep of randomly selecting two atoms of said single bred child member representation and randomly modifying a bond between said selected two atoms to provide one of said member representations to be reproduced within said next population.

18. The method to evolve said molecule as claimed in claim 8, wherein said step b) of selecting and changing includes substeps of selecting one of said selected number of said child member representations in accordance with a finite probability and of mutating said selected one child member representation of provide one of said member representations to be reproduced within said next population.

19. The method of evolve said molecule as claimed in claim 18, wherein said substep of mutating includes a first subsubstep of selecting an atom with randomly determined properties and adding said selected atom to said selected one child member representation to provide one of said member representations to be reproduced within said next population.

20. The method to evolve said molecule as claimed in claim 19, wherein said substep of mutating includes a second subsubstep of randomly selecting an atom of said selected one child member representation and removing it to provide one of said member representations to be reproduced within said next population.

21. The method to evolve said molecule as claimed in claim 20, wherein said substep of mutating includes a third subsubstep of selecting an atom of said selected one child member representation and replacing it with an atom of randomly determined properties to provide one of said member representations to be reproduced within said next population.

22. The method to evolve said molecule as claimed in claim 21, wherein said substep of mutating includes a fourth subsubstep of randomly selecting two atoms of said selected one child member representation and randomly modifying a bond between said selected two atoms to provide one of said member representations to be reproduced with said next population.

23. The method to evolve said molecule as claimed in claim 22, wherein said substep of mutating includes a fifth subsubstep of establishing of a table for storing finite probabilities for mutating in accordance with one of said first, second, third and fourth subsubsteps of mutating each selected one child member representation produced from one or more parent member representations of said present population and a sixth subsubstep of selecting from said table for each of said selected one child member representations one of said first, second, third and fourth subsubsteps to mutate each of said selected one child member representations produced from two parent member representations of said present population to provide said member representations to be reproduced within said next population.

24. The method to evolve said molecule as claimed in claim 1, wherein said comparing step a) comprises substeps of converting said set of desired properties into a digital property representation thereof, and of converting each member representation of said present population into a digital member representation thereof and comparing each of said digital member representations one at a time with said digital property representation to determine a similarity therebetween.

25. The method of evolve said molecule as claimed in claim 1, wherein said comparing step a) comprises substeps of converting said set of desired properties into a digital fingerprint thereof, and converting each member representation of said present population into a digital structural representation thereof and comparing each of said digital structural representations one at a time with said digital fingerprint to determine a metric therebetween.

26. The method to evolve said molecule as claimed in claim 25, wherein said set of desired properties is a molecular structure of said molecule.

27. The method to evolve said molecule as claimed in claim 26, wherein said comparing step a) implements a fitness function to determine a binding energy between each of said member representations of said present population and said set of desired properties, said comparing step a) comprises substeps of constructing a model of a binding site in accordance with said set of desired properties and of carrying out a series of conformational analyses on each of said member representations of said present population to determine said binding energy between each of said member representations and said digital fingerprint.

28. The method to evolve said molecule as claimed in claim 27, wherein said binding site forms a receptor pocket, said substep of constructing said model includes generating a plurality of spheres which fill said receptor pocket and of creating a digital representation of said plurality of spheres.

29. The method to evolve said molecule as claimed in claim 28, wherein said substep of said conformational analyses randomly measures geometric distances between said plurality of spheres and a molecular structure defined by each member representation of said present population and for providing for each of said conformational analyses said numerical value in terms of said binding energy.

30. The method to evolve said molecule as claimed in claim 27, wherein each member representation of said present population comprises electrical charges associated with a plurality of atoms making up its corresponding member molecule, and said substep of constructing said model includes defining those electrical charges associated with said atoms which comprise said binding site in accordance with said digited fingerprint.

31. The method to evolve said molecule as claimed in claim 30, wherein each of said conformational analyses determines an electrostatic interaction between said electrical charges associated with one of said member representations and said electrical charges associated with said binding site to provide a corresponding numerical value.

32. The method to evolve said molecule as claimed in claim 25, wherein said set of desired properties is a representation of a class of related molecules.

33. The method to evolve said molecule as claimed in claim 32, wherein there is further included a step of analyzing each molecule of said class to determine a presence of a common characteristic of the molecules in said class and for setting corresponding bits of said member representation if said common characteristic is determined to be present.

34. The method to evolve said molecule as claimed in claim 1, wherein said step a) of comparing comprises substeps of synthesizing an actual molecule for each member representation of said present population, of introducing a sample of an actual molecule having said set of desired properties and of assaying a binding energy between each of said synthesized molecules and said molecule to provide a corresponding set of numerical values.

35. The method to evolve said molecule as claimed in claim 1, wherein said step a) of comparing performs at least one fitness function wherein a fit between said set of desired properties and each member representation of said present population is determined to provide for each member representation a single fitness value.

36. The method to evolve said molecule as claimed in claim 35, wherein said step a) of comparing performs a plurality of fitness functions on each member representation of said present population, each of said plurality of fitness functions having a corresponding set of desired properties.

37. The method to evolve said molecule as claimed in claim 36, wherein each performance of said plurality of fitness functions provides a partial function value, and said partial function values are combined for each member representation of said present population.

38. The method to evolve said molecule as claimed in claim 37, wherein said partial function value for each fitness function is scaled to express said partial function values provided from said plurality of fitness functions in common units.

39. The method to evolve said molecule as claimed in claim 1, wherein said step b) of selecting provides member representations of said next population only from selected member representations of said present population.

40. The method to evolve said molecule as claimed in claim 1, wherein each population of said sequence of populations comprises a given number of said member representations.

* * * * *